US010758574B2

(12) United States Patent
Bhutani et al.

(10) Patent No.: US 10,758,574 B2
(45) Date of Patent: Sep. 1, 2020

(54) CARTILAGE CELLS WITH A HIGH REGENERATIVE POTENTIAL AND LOW IMMUNE RESPONSE FOR USE IN CELLULAR THERAPY

(71) Applicant: The Board of Trustees of the Leland Stanford Junior University, Stanford, CA (US)

(72) Inventors: Nidhi Bhutani, Fremont, CA (US); Jieun Lee, Menlo Park, CA (US); Sarah Taylor, Fremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 379 days.

(21) Appl. No.: 15/581,950

(22) Filed: Apr. 28, 2017

(65) Prior Publication Data

US 2017/0312316 A1 Nov. 2, 2017

Related U.S. Application Data

(60) Provisional application No. 62/328,754, filed on Apr. 28, 2016.

(51) Int. Cl.
*A61K 35/32* (2015.01)
*C12N 5/077* (2010.01)

(52) U.S. Cl.
CPC ............ *A61K 35/32* (2013.01); *C12N 5/0655* (2013.01); *C12N 2501/2301* (2013.01)

(58) Field of Classification Search
CPC .. A61K 35/32; A61K 35/545; C12N 2501/15; C12N 2501/155; C12N 2501/385; C12N 2501/602; C12N 2501/603; C12N 2501/604; C12N 2501/606; C12N 2506/13; C12N 2510/00; C12N 2513/00; C12N 2533/54; C12N 5/0696; C12N 2501/2301; C12N 5/0655
See application file for complete search history.

(56) References Cited

U.S. PATENT DOCUMENTS

| | | | |
|---|---|---|---|
| 7,622,108 B2 | 11/2009 | Collins et al. | |
| 8,808,697 B2 | 8/2014 | Zheng et al. | |
| 8,962,321 B2 | 2/2015 | Kimbrel et al. | |
| 2015/0275181 A1* | 10/2015 | D'Lima et al. | A61K 35/32 424/93.7 |

OTHER PUBLICATIONS

Xiaoming et al. (2014) Chinese Medical Journal 127(8): 1474-1481. (Year: 2014).*
Lee et al. (2016) Arthritis Research and Therapy 18: 292 (DOI 10.1186/s13075-016-1183-y) (Year: 2016).*
Grogan et al., Identification of Markers to Characterize and Sort Human Articular Chondrocytes With Enhanced In Vitro Chondrogenic Capacity, Arthritis & Rheumatism, vol. 56, No. 2, Feb. 2007, pp. 586-595 (Year: 2007).*
Taylor et al., Identification of Human Juvenile Chondrocyte-Specific Factors that Stimulate Stem Cell Growth, Tissue Engineering: Part A vol. 22, Nos. 7 and 8, 2016 (Year: 2016).*
Pruszak et al., CD15, CD24, and CD29 Define a Surface Biomarker Code for Neural Lineage Differentiation of Stem Cells, Stem Cells. Dec. 2009 ; 27(12): 2928-2940 (Year: 2009).*
Elghetany et al., Assessment of CD24 Expression on Bone Marrow Neutrophilic Granulocytes: CD24 Is a Marker for the Myelocytic Stage of Development, American Journal of Hematology 71:348-349, 2002 (Year: 2002).*
Adkisson et al. The potential of human allogenic juvenile chondrocytes for restoration of articular cartilage, Am J Sports Med. Jul. 2010 ; 38(7): 1324-1333 (Year: 2010).*
Lee et al. Early induction of a prechondrogenic population allows efficient generation of stable chondrocytes from human induced pluripotent stem cells, FASEB J. 29, 3399-3410, 2015 (Year: 2015).*
Farr et al. Clinical, Radiographic, and Histological Outcomes After Cartilage Repair With Particulated Juvenile Articular Cartilage, The American Journal of Sports Medicine, vol. 42, No. 6, 2014 (Year: 2014).*
McCormick et al. Treatment of Focal Cartilage Defects With a Juvenile Allogeneic 3-Dimensional Articular Cartilage Graft, Oper Tech Sports Med 21:95-99, 2013 (Year: 2013).*
Smeriglio et al., Comparative Potential of Juvenile and Adult Human Articular Chondrocytes for Cartilage Tissue Formation in Three-Dimensional Biomimetic Hydrogels, Tissue Engineering: Part A vol. 21, Nos. 1 and 2, 2015 (Year: 2015).*
Kreuz et al., Scaffold-assisted cartilage tissue engineering using infant chondrocytes from human hip cartilage, Osteoarthiritis and Cartilage 21 (2013), 1997-2005 (Year: 2013).*
Taylor et al. (2016) Identification of Human Juvenile Chondrocyte-Specific Factors that Stimulate Stem Cell Growth. Tissue Eng Part A. 22(7-8):645-653.
Lee et al. (2015) Early induction of a prechondrogenic population allows efficient generation of stable chondrocytes from human induced pluripotent stem cells. FASEB J. 29(8):3399-3410.

(Continued)

*Primary Examiner* — Louise W Humphrey
*Assistant Examiner* — Srikanth Patury
(74) *Attorney, Agent, or Firm* — Edward D. Grieff; Mintz, Levin, Cohn, Ferris, Glovsky and Popeo, P.C.

(57) ABSTRACT

Cell-based therapies for cartilage repair and regeneration selectively using chondrocytes carrying a CD24 surface marker are disclosed. In particular, chondrocytes carrying the CD24 surface marker have a high regenerative potential and low responsiveness to inflammatory cues. Since cartilage injuries as well as chronic cartilage degenerative conditions are often accompanied by a heightened inflammatory environment, cartilage cell populations carrying the CD24 surface marker, which are resistant to the inflammatory environment, provide more efficient cartilage repair. Thus, chondrocytes carrying the CD24 surface marker are useful in cell-based therapies for regenerating or repairing cartilage.

8 Claims, 40 Drawing Sheets

(56) References Cited

OTHER PUBLICATIONS

Kristiansen et al. (2004) Tumour biological aspects of CD24, a mucin-like adhesion molecule. J. Mol. Histol. 35(3):255-262.
Taguch et al. (2003) Pre-B cell antigen receptor-mediated signal inhibits CD24-induced apoptosis in human pre-B cells. J. Immunol. 170(1):252-260.
Li et al. (2004) CD24 expression on T cells is required for optimal T cell proliferation in lymphopenic host. J. Exp. Med. 200(8):1083-1089.
Nieoullon et al. (2007) Mouse CD24 is required for homeostatic cell renewal. Cell Tissue Res. 329(3):457-467.
Wang et al. (2007) A dinucleotide deletion in CD24 confers protection against autoimmune diseases. PLoS Genet. 3(4):e49.
Zhou et al. (2003) CD24 is a genetic modifier for risk and progression of multiple sclerosis. Proc. Natl. Acad. Sci. USA 100(25):15041-15046.
Hedbom et al. (2002) Molecular aspects of pathogenesis in osteoarthritis: the role of inflammation. Cell Mol. Life Sci. 59(1):45-53.

\* cited by examiner

… (1)

CARTILAGE CELLS WITH A HIGH REGENERATIVE POTENTIAL AND LOW IMMUNE RESPONSE FOR USE IN CELLULAR THERAPY

CROSS-REFERENCE TO RELATED APPLICATION

This application claims benefit under 35 U.S.C. § 119(e) of provisional application 62/328,754, filed Apr. 28, 2016, which application is hereby incorporated by reference in its entirety.

TECHNICAL FIELD

The present invention pertains generally to tissue engineering and regenerative medicine. In particular, the invention relates to cell-based therapies for cartilage repair and regeneration selectively using chondrocytes carrying a CD24 surface marker.

BACKGROUND

Cartilage degenerative diseases like rheumatoid arthritis (RA) and osteoarthritis (OA) have age, obesity and inflammation as causal risk factors however the precise molecular mechanisms underlying these risk factors are ill understood. No disease-modifying drug is available for OA while the drugs available for RA are not equally effective for all patients. An increased molecular understanding of the causal factors will therefore be beneficial for both diseases.

Very few studies have systematically evaluated the age-dependent changes in human tissues including cartilage due to the limited availability. Such studies are particularly pertinent for cartilage since cartilage regeneration is inefficient even in healthy young adults often leading to OA although pediatric populations demonstrate superior cartilage repair. Recently, allogeneic juvenile cartilage (from donors less than 13 years of age) has even been successfully utilized for repair of focal cartilage defects. Upon phenotypic and functional characterization of juvenile and adult chondrocytes, it was found that juvenile chondrocytes demonstrated increased cell proliferation and ECM generation as compared to the adult chondrocytes. The molecular factors responsible for these functional differences that define the regenerative capacity of juvenile and adult chondrocytes have however not been characterized.

Another key question that remains unanswered is how age-related changes modulate the cell and tissue-specific response to inflammation. Inflammaging, i.e., a systemic upregulation of inflammatory cues with aging, is a well-documented phenomenon. For example, plasma levels of the pro-inflammatory cytokine IL-6 are low in young adults and begin to increase in healthy people at about 50-60 years of age (Ershler (1993) J. Am. Geriatr. Soc. 41(2):176-181). Inflammaging is associated with many forms of age-related pathologies, such as neurodegeneration, atherosclerosis, metabolic syndrome, diabetes mellitus and musculoskeletal system (i.e. osteoporosis, OA and RA). However, since age dependent tissue-specific changes are not well understood, it remains unclear whether the age-related changes in tissues render them increasingly susceptible to the inflammaging cues thereby leading to a synergistic increase in inflammation-mediated damage in aging tissues.

There remains a need for improved cell-based therapies for repair and regeneration of cartilage for treating bodily injuries and diseases involving cartilage degeneration.

SUMMARY

The invention relates to cell-based therapies using chondrocytes carrying a CD24 surface marker for repair and regeneration of damaged cartilage for treating bodily injuries and degenerative diseases.

In one aspect, the invention includes a method of enriching for chondrocytes having regenerative potential for cartilage repair, the method comprising: a) providing a sample comprising chondrocytes; and b) enriching for chondrocytes carrying a CD24 surface marker. Enriching for chondrocytes carrying a CD24 surface marker can be accomplished, for example, by performing fluorescence-activated cell sorting (FACS), magnetic-activated cell sorting (MACS), single cell sorting, or affinity chromatography. In certain embodiments, the chondrocytes are selected from the group consisting of neonatal chondrocytes, juvenile chondrocytes, adult chondrocytes, or chondrocytes derived from stem cells (e.g., induced pluripotent stem cells). In one embodiment, the chondrocytes are from a human subject.

In another aspect, the invention includes a method of treating a subject for cartilage damage or loss, the method comprising: a) providing a sample comprising chondrocytes; b) isolating chondrocytes carrying a CD24 surface marker from the sample; and c) administering a therapeutically effective amount of the chondrocytes carrying the CD24 surface marker to the subject. The cartilage damage or loss may be caused by a traumatic injury or a disease involving cartilage degeneration (e.g., rheumatoid arthritis or osteoarthritis). In one embodiment, the method further comprises culturing the chondrocytes under conditions in which the chondrocytes proliferate before administering the chondrocytes to the subject.

In certain embodiments, the chondrocytes carrying the CD24 surface marker are isolated from the sample using fluorescence-activated cell sorting (FACS), magnetic-activated cell sorting (MACS), single cell sorting, affinity chromatography, or microfluidic cell separation techniques.

In another embodiment, the chondrocytes are selected from the group consisting of neonatal chondrocytes, juvenile chondrocytes, adult chondrocytes, or chondrocytes derived from stem cells (e.g., pluripotent stem cells). The chondrocytes may be xenogeneic, autologous, or allogeneic.

In another aspect, the invention includes a method of generating new cartilage in a subject, the method comprising administering an effective amount of substantially purified chondrocytes carrying a CD24 surface marker to the subject. Preferably, the new cartilage is produced from the chondrocytes in an amount effective for treating the subject for a traumatic injury or a disease involving cartilage degeneration. In one embodiment, the chondrocytes are selected from the group consisting of neonatal chondrocytes, juvenile chondrocytes, adult chondrocytes, or chondrocytes derived from stem cells (e.g., pluripotent stem cells). In another embodiment, the chondrocytes are xenogeneic, autologous, or allogeneic. In a further embodiment, the method further comprises culturing the chondrocytes under conditions in which the chondrocytes proliferate before administering the chondrocytes to the subject.

Compositions comprising chondrocytes carrying a CD24 surface marker (e.g., substantially purified or enriched for chondrocytes carrying the CD24 surface marker) may be administered by any suitable method, such as by injection or implantation locally into an area of cartilage damage or loss, such as a damaged joint of a subject.

In another aspect, the invention includes a kit comprising a composition comprising substantially purified chondrocytes carrying a CD24 surface marker for generating new cartilage. The kit may also comprise means for delivering the composition to a subject and instructions for treating a traumatic injury or a disease involving cartilage degeneration.

These and other embodiments of the subject invention will readily occur to those of skill in the art in view of the disclosure herein.

BRIEF DESCRIPTION OF THE FIGURES

FIGS. 5A-5C shows NFκb gene expression by q-PCR for hiChondrocytes (FIG. 5A), juvenile chondrocytes (FIG. 5B), and adult chondrocytes (FIG. 5C). FIGS. 5D-5F show a reporter luciferase assay indicating that loss of CD24 increases NFκb activity in chondrocytes, including hiChondrocytes (Batch #16) (FIG. 5E), juvenile chondrocytes (24 weeks) (FIG. 5F), and adult chondrocytes (27F) (FIG. 5G). FIG. 5D shows a schematic of the assay design (*p<0.01).

FIG. 7A shows shCD24 knockdown in chondrocytes. Three of the five shRNAs tested (sh1, sh2 and sh3) showed 80% or greater knockdown of CD24 expression. FIGS. 7B-7D show CD24 cDNA expression in shCD24 knockdown-chondrocytes, including hiChondrocytes (FIG. 7B), juvenile chondrocytes (FIG. 7C), and adult chondrocytes (FIG. 7D). FIG. 7E shows results of flow cytometry identifying that CD24 positive cells were reduced by shRNA knockdown.

FIG. 10A shows a schematic of the assay design. FIG. 10B shows the results in juvenile chondrocytes (24 weeks) and adult chondrocytes (27F) (Batch #16), (*p<0.01).

DETAILED DESCRIPTION

Figure 1A:
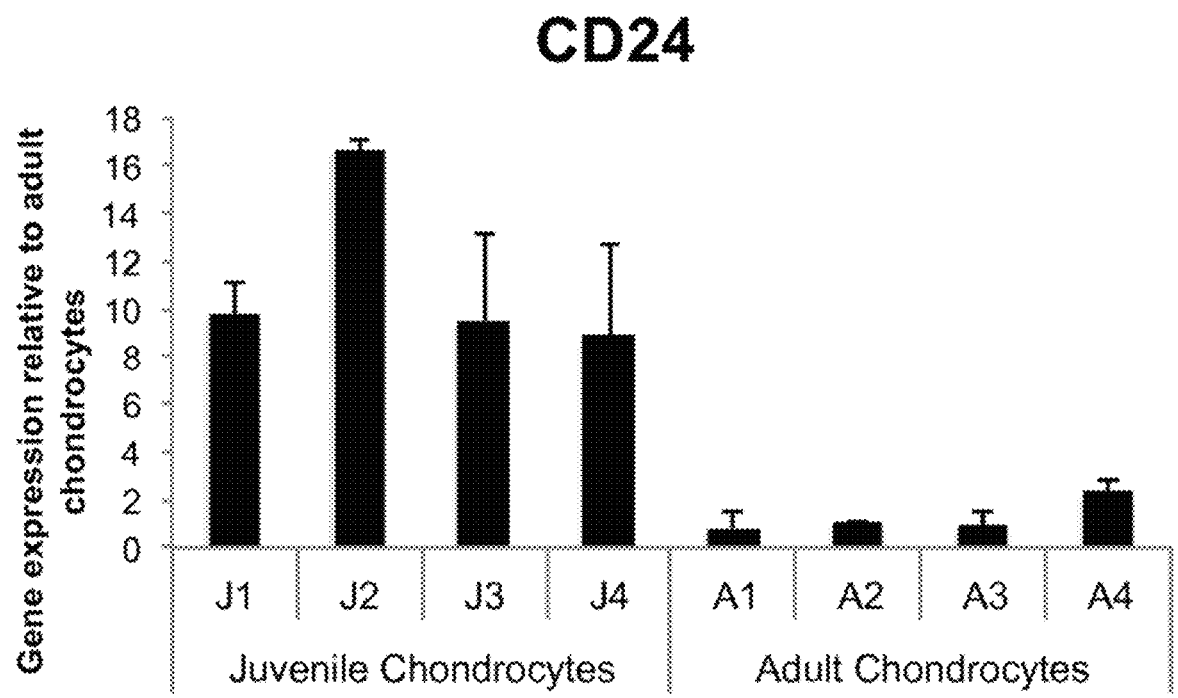
FIG. 1A shows gene expression of CD24 is high in juvenile chondrocytes (J1-J4: 24 weeks, 18 month, 6 month, 6 years) compared to adult chondrocytes (A1-A4; 18M, 25M, 27F, 39F).

The practice of the present invention will employ, unless otherwise indicated, conventional methods of medicine, cell biology, chemistry, biochemistry, molecular biology and recombinant DNA techniques, and immunology, within the skill of the art. Such techniques are explained fully in the literature. See, e.g., G. Vunjak-Novakovic and R. I. Freshney *Culture of Cells for Tissue Engineering* (Wiley-Liss, 1$^{st}$ edition, 2006); *Arthritis Research: Methods and Protocols*, Vols. 1 and 2: (Methods in Molecular Medicine, Cope ed., Humana Press, 2007); *Cartilage Tissue Engineering: Methods and Protocols* (Methods in Molecular Biology, P. M. Doran ed., Humana Press, 2015); *Tissue Engineering of Cartilage and Bone* (Novartis Foundation Symposia, Wiley, 2010); *Cartilage and Osteoarthritis* (Methods in Molecular Medicine, M. Sabatini P. Pastoureau, and F. De Ceuninck eds., Humana Press; 2004); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); and Sambrook et al., *Molecular Cloning: A Laboratory Manual* (3$^{rd}$ Edition, 2001).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a chondrocyte" includes a mixture of two or more chondrocytes, and the like.

The term "about," particularly in reference to a given quantity, is meant to encompass deviations of plus or minus five percent.

The term "chondrocyte" refers to any chondrocyte derived from a vertebrate subject suitable for transplantation into the same or a different subject. The chondrocyte may be xenogeneic, autologous, or allogeneic. The chondrocyte can be a primary cell obtained directly from a vertebrate subject. The chondrocyte may also be a cell derived from the culture and expansion of a cell obtained from a subject. For example, the chondrocyte may be a neonatal chondrocyte, juvenile chondrocyte, adult chondrocyte, or a chondrocyte derived from a stem cell (i.e., induced to differentiate into a chondrocyte).

As used herein, the term "cell viability" refers to a measure of the amount of cells that are living or dead, based on a total cell sample. High cell viability, as defined herein, refers to a cell population in which greater than 85% of all cells are viable, preferably greater than 90-95%, and more preferably a population characterized by high cell viability containing more than 99% viable cells.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

"Transplant" refers to the transfer of a cell, tissue, or organ to a subject from another source. The term is not limited to a particular mode of transfer. Cells may be transplanted by any suitable method, such as by injection or surgical implantation.

The term "arthritis" includes, but is not limited to, osteoarthritis, rheumatoid arthritis, lupus-associated arthritis, juvenile idiopathic arthritis, reactive arthritis, enteropathic arthritis and psoriatic arthritis.

The term "disease involving cartilage degeneration" includes any disease or disorder involving cartilage and/or joint degeneration. The term "disease involving cartilage degeneration" includes disorders, syndromes, diseases, and injuries that affect spinal discs or joints (e.g., articular joints) in animals, including humans, and includes, but is not limited to, arthritis, chondrophasia, spondyloarthropathy, ankylosing spondylitis, lupus erythematosus, relapsing polychondritis, and Sjogren's syndrome.

By "therapeutically effective dose or amount" of chondrocytes carrying a CD24 surface marker is intended an amount that, when administered as described herein, brings about a positive therapeutic response in a subject having cartilage damage or loss, such as an amount that results in the generation of new cartilage at a treatment site (e.g., a damaged joint). For example, a therapeutically effective dose or amount could be used to treat cartilage damage or loss resulting from a traumatic injury or a degenerative disease, such as arthritis or other disease involving cartilage degeneration. Preferably, a therapeutically effective amount restores function and/or relieves pain and inflammation associated with cartilage damage or loss. The exact amount required will vary from subject to subject, depending on the species, age, and general condition of the subject, the severity of the condition being treated, mode of administration, and the like. An appropriate "effective" amount in any individual case may be determined by one of ordinary skill in the art using routine experimentation, based upon the information provided herein.

"Substantially purified" refers to isolation of a substance or cell (e.g., chondrocyte) such that the substance or cell comprises the majority percent of the sample in which it resides. Typically in a sample, a substantially purified component comprises 90%-92%, 93-95%, 96%-98%, or 99%-100% of the sample or any percent within these ranges, including at least 90%, 91%, 92%, 93%, 94%, 95%, 96%, 97%, 98%, 99%, or 100% of the sample. Techniques for purifying cells of interest are well-known in the art and include, for example, fluorescence-activated cell sorting (FACS), magnetic-activated cell sorting (MACS), single cell sorting, affinity chromatography, microfluidic cell separation, and sedimentation according to density.

The terms "subject," "individual" or "patient" are used interchangeably herein and refer to a vertebrate, preferably a mammal. By "vertebrate" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery that the cell surface marker CD24 can be used to isolate cartilage cells that have a high regenerative potential and low responsiveness to inflammatory cues. The inventors have shown that CD24 exhibits higher expression in both juvenile chondrocytes and chondrocytes derived from human induced pluripotent stem cells (hiPSC) than adult chondrocytes (Example 1). In addition, CD24 modulates NFκb activity and dampens the response to inflammatory cues. Since cartilage injuries as well as chronic cartilage degenerative conditions are often accompanied by a heightened inflammatory environment, cartilage cell populations carrying the CD24 surface marker, which are resistant to the inflammatory environment, have the advantage of having the ability to provide more efficient cartilage repair. Thus, chondrocytes carrying the CD24 surface marker are useful in cell-based therapies for regenerating, replacing, or repairing cartilage.

In order to further an understanding of the invention, a more detailed discussion is provided below regarding cell-based therapies using chondrocytes carrying the CD24 surface marker for treating diseases and conditions causing cartilage damage or loss.

A. Chondrocytes Carrying a CD24 Surface Marker for Cellular Therapy

Chondrocytes carrying the CD24 surface marker have been shown to have superior regenerative potential for cartilage repair. Thus, in one aspect, the invention includes a method of treating a subject for cartilage damage or loss comprising administering a therapeutically effective amount of chondrocytes carrying the CD24 surface marker to the subject.

Samples comprising neonatal chondrocytes, juvenile chondrocytes, adult chondrocytes, or chondrocytes derived from stem cells (i.e., induced to differentiate into chondrocytes) may be used in the methods of the invention. The chondrocytes may be xenogeneic, autologous, or allogeneic. The chondrocytes used in treatment can be obtained directly from the subject undergoing treatment, or a donor, a culture of cells from a donor, or from established cell culture lines. Chondrocytes may be obtained from the same or a different species than the subject to be treated, but preferably are of the same species, and more preferably of the same immunological profile as the subject. Such cells can be obtained, for example, from a sample of cartilage (e.g. biopsy) collected from the subject to be treated, or a relative or matched donor.

Alternatively, chondrocytes can be derived from stem cells. The stem cells used to produce chondrocytes can include stem cells from embryos, umbilical cord, or adult tissues, or induced pluripotent stem cells. In order to induce differentiation into chondrocytes, the stem cells are cultured in the presence of various factors such as Wnt3a, activin A, fibroblast growth factor 2 (FGF2), bone morphogenetic protein (BMP)-4, and growth differentiation factor 5 (GDF5). In addition, p160-Rho-associated coil kinase (ROCK) inhibitor Y27632 and neurotrophin (NT)-4 can be used to promote stem cell survival, and follistatin can be used to reduce endodermal gene expression. See, e.g., Lee et al. (2015) FASEB J 29(8):3399-3410, Oldershaw et al. (2010) Nat. Biotechnol. 28:1187-1194; herein incorporated by reference in their entireties).

Chondrocytes carrying the CD24 surface marker can be isolated from samples containing mixed populations of cells according to any technique known in the art. For example, chondrocytes carrying the CD24 surface marker can be separated from other chondrocytes (i.e., not expressing CD24) and other cell types using methods including, but not limited to, fluorescence-activated cell sorting (FACS), magnetic-activated cell sorting (MACS), single cell sorting, affinity chromatography, and microfluidic cell separation techniques. For a review of cell sorting and separation techniques, see, e.g., *Flow Cytometry and Cell Sorting* (Springer Lab Manuals, Andreas Radbruch ed., Springer, $2^{nd}$ edition, 2000); *Cell Separation: A Practical Approach* (Practical Approach Series, by D. Fisher, G. E. Francis, and D. Rickwood eds., Oxford University Press, 1999); Dainiak et al. (2007) Adv Biochem Engin/Biotechnol 106:1-18; Ibrahim et al. (2007) Adv Biochem Eng Biotechnol 106:19-39; Plouffe et al. (2014) Anal Chem. 86(23):11481-11488, Lenshof et al. (2010) Chem Soc Rev 39(3):1203-1217; herein incorporated by reference in their entireties.

In particular, differential antibody binding or immunoselection techniques can be used to separate desired cells from a cell population based on their surface antigens (e.g., CD24 molecules). In immunoselection techniques, the antibody is typically detectably labeled by covalent linkage to a molecule, such as a fluorophore (e.g., immunofluorescent technology, FACS) or a magnetic particle (e.g., immunomagnetic technology, MACS). For affinity chromatography, a matrix comprising an antibody (i.e., immunoadsorbent) specific for a surface antigen can be used to bind cells. Specific anti-CD24 antibodies can be used for the positive selection of the CD24 surface antigen on chondrocytes. Alternatively or in addition, negative selection methods can be used to deplete non-desired cells (e.g., chondrocytes not carrying the CD24 surface antigen and other cell types) from a sample. Preferably, compositions comprising substantially purified chondrocytes carrying the CD24 surface marker are used in treatment of a subject for cartilage damage or loss, such as caused by a traumatic injury or a disease involving cartilage degeneration.

Compositions comprising chondrocytes carrying the CD24 surface marker may further include one or more factors, such as nutrients, extracellular matrix (ECM) components, cytokines, growth factors, antibiotics, anti-oxidants, or immunosuppressive agents, which may be added, for example, to improve cell function or viability. Compositions may also further comprise a pharmaceutically acceptable carrier.

Exemplary ECM components include proteoglycans (e.g., chondroitin sulfate, heparan sulfate, and keratan sulfate), non-proteoglycan polysaccharides (e.g., hyaluronic acid), a fiber (e.g., collagen and elastin), and any other ECM components (e.g., fibronectin and laminin).

Exemplary growth factors include, fibroblast growth factor (FGF), insulin-like growth factor (IGF), transforming growth factor beta (TGF-β), epiregulin, epidermal growth factor (EGF), endothelial cell growth factor (ECGF), nerve growth factor (NGF), leukemia inhibitory factor (LIF), bone morphogenetic protein-4 (BMP-4), hepatocyte growth factor (HGF), vascular endothelial growth factor-A (VEGF-A), and cholecystokinin octapeptide.

Exemplary immunosuppressive agents are well known and may be steroidal (e.g., prednisone) or non-steroidal (e.g., sirolimus (Rapamune, Wyeth-Ayerst Canada), tacrolimus (Prograf, Fujisawa Canada), and anti-IL2R daclizumab (Zenapax, Roche Canada). Other immunosuppressant agents include 15-deoxyspergualin, cyclosporin, methotrexate, rapamycin, Rapamune (sirolimus/rapamycin), FK506, or Lisofylline (LSF).

One or more pharmaceutically acceptable excipients may also be included. Exemplary excipients include, without limitation, carbohydrates, inorganic salts, antimicrobial agents, antioxidants, surfactants, buffers, acids, bases, and combinations thereof.

For example, an antimicrobial agent for preventing or deterring microbial growth may be included. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof. Antibmicrobial agents also include antibiotics that can also be used to prevent bacterial infection. Exemplary antibiotics include amoxicillin, penicillin, sulfa drugs, cephalosporins, erythromycin, streptomycin, gentamicin, tetracycline, chlarithromycin, ciproflozacin, azithromycin, and the like. Also included are antifungal agents such as myconazole and terconazole.

Various antioxidants can also be included, such as molecules having thiol groups such as reduced glutathione (GSH) or its precursors, glutathione or glutathione analogs, glutathione monoester, and N-acetylcysteine. Other suitable anti-oxidants include superoxide dismutase, catalase, vitamin E, Trolox, lipoic acid, lazaroids, butylated hydroxyanisole (BHA), vitamin K, and the like.

Excipients suitable for injectable compositions include water, alcohols, polyols, glycerin, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

Acids or bases can also be present as an excipient. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The pharmaceutical preparations herein can also be housed in a syringe, an implantation device, or the like, depending upon the intended mode of delivery and use. Preferably, the compositions comprising chondrocytes carrying a CD24 surface marker are in unit dosage form, meaning an amount of the chondrocytes appropriate for a single dose, in a premeasured or pre-packaged form.

B. Administration

Compositions comprising chondrocytes carrying a CD24 surface marker can be used for treating a subject for cartilage damage or loss, such as caused by a traumatic injury or a disease involving tissue degeneration. At least one therapeutically effective cycle of treatment with a composition comprising chondrocytes carrying a CD24 surface marker will be administered to a subject for treatment of a subject for cartilage damage or loss.

Diseases involving cartilage degeneration include disorders, syndromes, diseases, and injuries that affect spinal discs or joints (e.g., articular joints) in animals, including humans, and include, but are not limited to, arthritis, including osteoarthritis, rheumatoid arthritis, lupus-associated arthritis, juvenile idiopathic arthritis, reactive arthritis, enteropathic arthritis and psoriatic arthritis, chondrophasia, spondyloarthropathy, ankylosing spondylitis, lupus erythematosus, relapsing polychondritis, and Sjogren's syndrome.

By "therapeutically effective dose or amount" of chondrocytes carrying a CD24 surface marker is intended an amount that, when administered as described herein, brings about a positive therapeutic response in a subject having cartilage damage or loss, such as an amount that results in the generation of new cartilage at a treatment site (e.g., a damaged joint). For example, a therapeutically effective dose or amount could be used to treat cartilage damage or loss resulting from a traumatic injury or a degenerative disease, such as arthritis or other disease involving cartilage degeneration. Preferably, a therapeutically effective amount restores function and/or relieves pain and inflammation associated with cartilage damage or loss.

In certain embodiments, multiple therapeutically effective doses of compositions comprising chondrocytes carrying a CD24 surface marker and/or one or more other therapeutic agents, such as other drugs for treating a degenerative disease, such as arthritis or other disease involving cartilage degeneration, or other medications will be administered. Compositions for transplanting chondrocytes carrying a CD24 surface marker are typically, though not necessarily, administered by injection or surgical implantation into a region requiring cartilage replacement or repair. For example, compositions capable of producing new cartilage in a subject can be administered locally into an area of cartilage damage or loss, such as a damaged joint or other suitable treatment site of the subject.

Those of ordinary skill in the art will appreciate which conditions chondrocytes carrying a CD24 surface marker can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Chondrocytes carrying a CD24 surface marker can be administered alone or in combination with one or more other therapeutic agents, such as drugs for treating inflammation or pain, including non-steroidal anti-inflammatory agents (NSAIDs) such as ibuprofen or aspirin (which reduce swelling and alleviate pain); disease-modifying anti-rheumatic drugs (DMARDs) such as methotrexate; 5-aminosalicylates (sulfasalazine and the sulfa-free agents); corticosteroids; immunomodulators such as 6-mercaptoputine ("6-MP"), azathioprine ("AZA"), cyclosporines, and biological response modifiers such as REMICADE (infliximab) and ENBREL (etanercept); fibroblast growth factors; platelet derived growth factors; enzyme blockers such as ARAVA (leflunomide); and/or a cartilage protecting agent such as hyaluronic acid, glucosamine, chondroitin, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day. Pharmaceutical compositions comprising chondrocytes carrying a CD24 surface marker and other agents may be administered using the same or different routes of administration in accordance with any medically acceptable method known in the art.

Chondrocytes carrying a CD24 surface marker can be administered prior to, concurrent with, or subsequent to other agents. If provided at the same time as other agents, chondrocytes carrying a CD24 surface marker can be provided in the same or in a different composition. Thus, chondrocytes carrying a CD24 surface marker and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising chondrocytes carrying a CD24 surface marker and a dose of a pharmaceutical composition comprising at least one other agent, such as another drug for treating inflammation or pain, which in combination comprise a therapeutically effective dose, according to a particular dosing regimen. Similarly, chondrocytes carrying a CD24 surface marker and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

C. Kits

Substantially purified chondrocytes carrying a CD24 surface marker may be included in a kit. The kit may comprise one or more containers holding the chondrocytes, and optionally other components such as media for culturing cells, growth factors, ECM components, antibiotics, and the like. Suitable containers for the compositions include, for example, bottles, vials, syringes, and test tubes. Containers can be formed from a variety of materials, including glass or plastic. A container may have a sterile access port (for example, the container may be a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions for methods of treating cartilage damage or loss, such as caused by a traumatic injury or a disease involving cartilage degeneration. The package insert can be an unapproved draft package insert or can be a package insert approved by the Food and Drug Administration (FDA) or other regulatory body.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

CD24 Enrichment in Neonatal Cartilage Reduces Susceptibility to Inflammation in an NF-κB Dependent Manner Introduction Diseases associated with human cartilage (including rheumatoid arthritis and osteoarthritis) have manifested age, mechanical stresses and inflammation as the leading causal and risk factors. Although inflamm-aging, i.e., upregulation of the inflammatory processes upon aging is well documented in multiple tissues, a detailed molecular understanding of how aging affects the tissue-specific response to inflammation per se is lacking. In this study, we report that Cluster of differentiation 24 (CD24) expression modulates response to inflammatory cues in human chondrocytes. Utilizing global gene expression profiling, we identified CD24 to be a cell-surface marker differentially enriched in hiPSC-derived chondrocytes (neonatal) and juvenile chondrocytes as compared to adult chondrocytes. Interestingly, CD24 expression in chondrocytes caused a differential response to cytokine-induced inflammation, with the $CD24^{high}$ neonatal chondrocytes being resistant to IL-1β treatment as compared to $CD24^{low}$ adult chondrocytes. CD24 inhibits NFκβ activation as an acute loss of CD24 via silencing led to an increase in Nfκβ activation and subsequent inflammatory and catabolic gene expression both in the absence and presence of IL-1β. We have therefore identified CD24 as a novel regulator of inflammatory response in cartilage that is altered during development and aging. Targeting inflammatory modulators like CD24 in cartilage could be a new therapeutic axis for degenerative diseases like RA and OA.

Methods and Materials

Chondrocyte Isolation and Culture.

Juvenile articular chondrocytes—24 weeks fetus (designated as J1), 6 years (J2), 6 months (J3) and 18 months (J4) were purchased from Lonza (Clonetics, Lonza Walkersville, Inc.) and cultured in Chondrocyte Growth Medium (Clonetics CGM, Lonza Walkersville, Inc.). Human adult articular chondrocytes were harvested from grossly normal cartilage pieces discarded during notchplasty or debridement from patients with no prior history of OA—female 27 year-old (A1), male 35 year-old (A2) and male 18 year-old (A3), and female 39 year-old (A4) undergoing Anterior Cruciate Ligament reconstruction under protocols approved by human subjects Institutional Review Board of Stanford University. Cartilage was dissected and the chondrocytes were dissociated from the matrix as described previously (Rueda et al. (2008) J. Rheumatol. 35(5):850-854). Chondrocytes were cultured in high density monolayers using Dulbecco's Modified Eagle's Medium (Thermo Scientific, Inc.) supplemented with 25 mg/mL ascorbate, 2 mM L-glutamine, 1% pen/strep antibiotics and 10% FBS (Invitrogen) at 37° C.

Flow Cytometry.

Cells were dissociated to a single-cell suspension using TrypLE (Life Technologies) and fixed in BD Cytofix buffer (BD Biosciences) for 20 minutes at room temperature. To permeabilize the cells, cells were washed and incubated with BD Permeabilization/Wash buffer (BD Biosciences) at $1\times10^7$ cells per 1 mL for 10 minutes. Cells were stained by incubating with anti-human CD24-PE (BD Biosciences) for 30 minutes. The antibody was diluted according to manufacturer's instruction. Stained cells were scanned using a LSR II flow cytometer and analyzed with FlowJo software.

Quantitative Real-Time PCR.

RNA was isolated with the RNeasy kit. First-strand cDNA was primed with oligo (dT) primers and qPCR was performed with Taqman primer sets from Applied Biosystems (Foster City, Calif.). Relative expression levels were normalized to GAPDH and 18 s and calculated using the 2-ΔCt method.

Lentivirus Preparation and Chondrocyte Transduction.

HEK293FT cells were plated at a density of $6\times10^6$ cells and transfected after 24 hours with 7.5 μg of VSV-G (p633, envelope protein), 7.5 μg of TAT, 7.5 μg of REV, 30 μg of Gag/Pol and 15 μg of CD24 short hairpin RNA (Sigma, SHCLNG-NM_013230) with Lipofectamine. Lentiviral solutions were collected after 48 hours and chondrocytes were transduced.

For CD24, the shRNAs sh1, sh2, and sh3 were used for a significant mRNA and protein knockdown. The non-target sequence used was p1.

IL-1b Treatment.

Chondrocytes and hiChondrocytes were plated at $5\times10^5$ cells per well in duplicates in 6-well plates. After 24 hours, cells were treated with control or IL-1b (10 ng/ml) in complete media for 2 days.

NF-κB Luciferase Assay.

Chondrocytes ($3\times10^5$/well) were subjected to either shNT or shCD24 infection with or without IL-1b (10 ng/ml). Cells were transfected with pNF-κB-Luc (Agilent Technologies, Santa Clara, Calif.) and pFC-MEKK as a positive control plasmid by using Fugene 6 (Promega, Madison, Wis.) and after 24 hours, cells were assayed using the Bright-Glo Luciferase Assay System (Promega) with a luminometer.

Statistical Analyses.

Statistical significance of data was determined by applying a two-tailed Student test to values obtained from at least three independent experiments.

Results

Figure 1B:
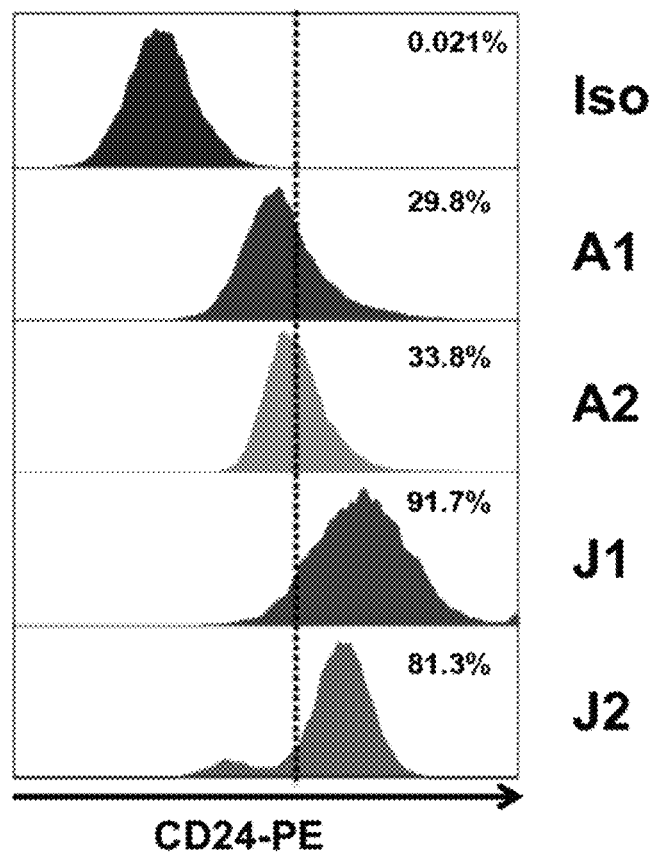
FIG. 1B shows a flow cytometry analysis showing that the population of CD24 positive cells is high in juvenile chondrocytes of 24 weeks and 18 month, 91.7% and 81.3%, respectively.

CD24 Expression is High in Juvenile Chondrocytes and hiChondrocytes Compared to Adult Chondrocytes We previously compared the molecular differences between the juvenile and adult articular chondrocytes by utilizing exon microarrays to determine their global gene expression profiles. Gene expression profiling was performed on three distinct human juvenile and adult chondrocyte samples and 600 genes were identified to be differentially upregulated in juvenile chondrocytes compared to adult chondrocytes (Taylor et al., paper in revision). Out of the identified factors, CD24 was a cell-surface receptor that showed 8-10-fold increased expression in juvenile chondrocytes as compared to the adult chondrocytes. To validate the differential enrichment of CD24 in Juvenile chondrocytes, we examined CD24 expression at a transcript level by quantitative PCR as well as at a single cell protein level utilizing FACS analyses (FIGS. 1A, 1B). Gene expression analyses on Juvenile and adult articular chondrocytes from four different donors each (see methods) confirmed an 8-10-fold increase in CD24 expression in the juvenile chondrocytes compared to the adult chondrocytes (FIG. 1A). Juvenile and adult chondrocytes from two donors each were further utilized for the single cell flow cytometry analyses. FACS analyses demonstrated that the juvenile chondrocytes consisted of a uniformly $CD24^{high}$ population (81-92%).

Figure 1C:
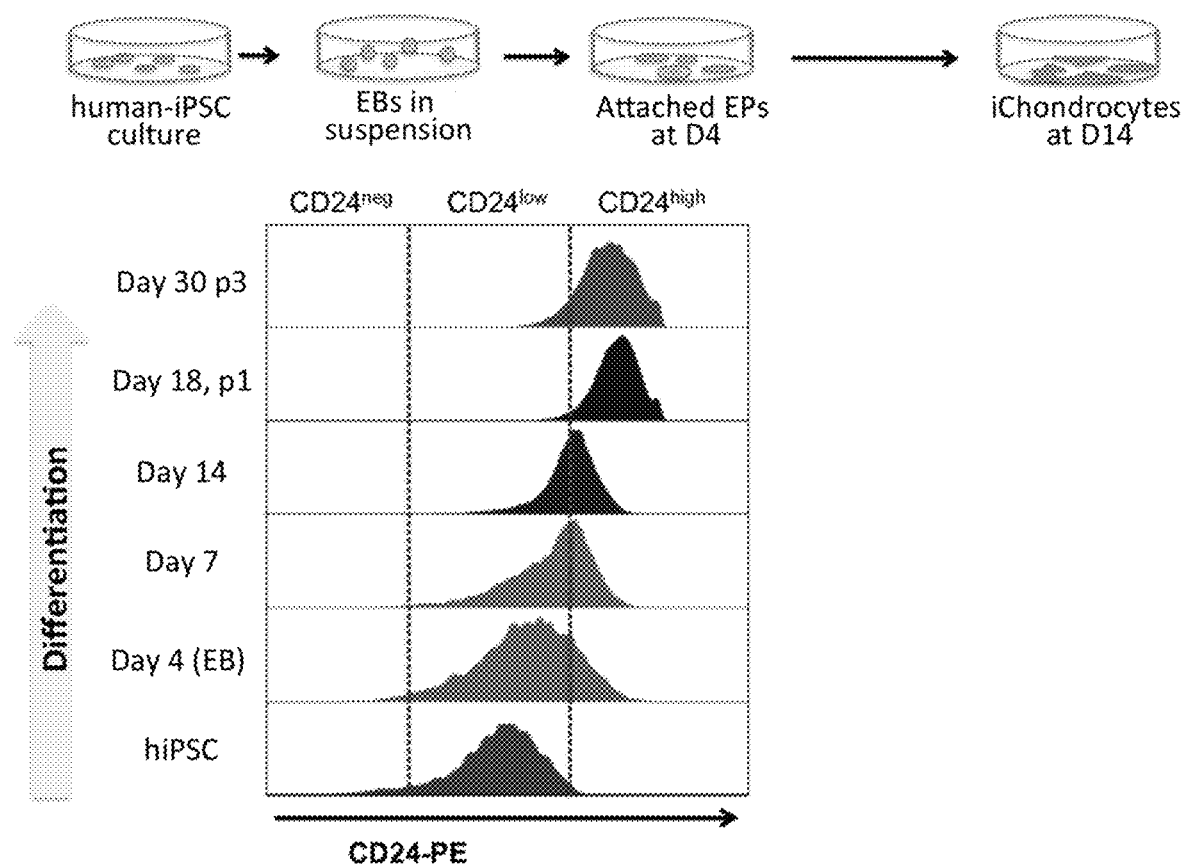
FIG. 1C shows that a CD24 positive cell population is gradually increased during chondrocyte differentiation (Day4-Day30) from hiPSCs.
Figure 1D:
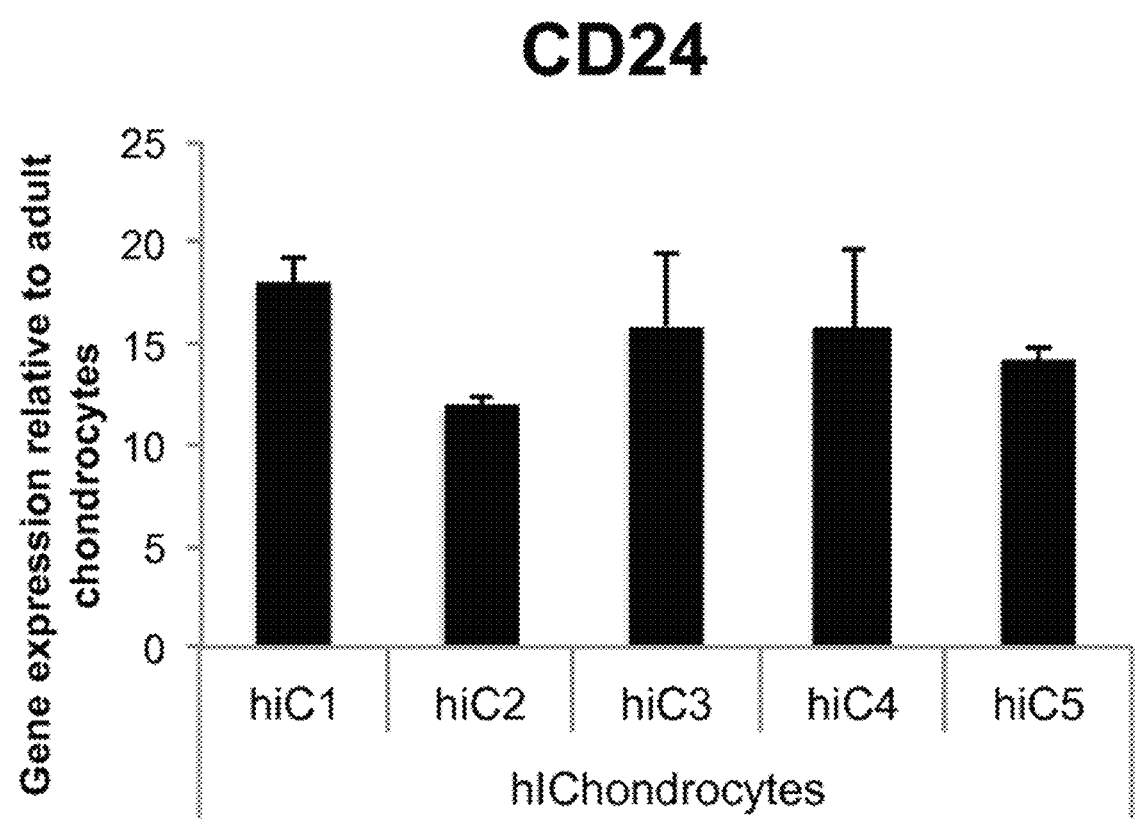
FIG. 1D shows that gene expression of CD24 is 15-fold higher in hiChondrocytes (hiC1-hiC5) compared to adult chondrocytes (27F).

The majority of the adult chondrocytes on the other hand showed a lower level of CD24 expression with only a small population (30-34%) being $CD24^{low}$ (FIG. 1B). Since CD24 appeared to mark neonatal/juvenile chondrocytes, we next assessed CD24 expression in human induced pluripotent stem cells (hiPSCs) and the hiPSC-derived chondrocytes (hiChondrocytes). We have previously established methods to differentiate hiPSC into articular-like chondrocytes (hiChondrocytes) and characterized the chondrogenic phenotype of the hichondrocytes in terms of gene and protein expression as well as their ability to engineer cartilage in vitro and in vivo (Lee J, et al. (2015) FASEB J. 29(8):3399-3410). We therefore hypothesized that these hichondrocytes will mimic developmentally younger chondrocytes and may have enriched levels of CD24. To test this hypothesis, we investigated CD24 expression during differentiation of hiPSC to chondrocytes in vitro at days 4, 7, 14, 18 and 20 after the initiation of differentiation. Interestingly, although hiPSC demonstrated low levels of CD24 as has been previously reported, the intensity of CD24 expression gradually increased during chondrogenic differentiation with the hichondrocytes consisting of a uniformly $CD24^{high}$ population after differentiation and early cell passages (FIG. 1C). Upon comparing CD24 gene expression in five biological replicates of independently derived hiChondrocytes to adult chondrocytes, a 10-18-fold increase was consistently observed demonstrating that the hichondrocytes were similar to the neonatal/juvenile chondrocytes in terms of CD24 expression (FIG. 1D). Collectively, these observations confirmed that CD24 is a cell surface receptor enriched in neonatal and juvenile chondrocytes as compared to adult chondrocytes.

Figure 2A:
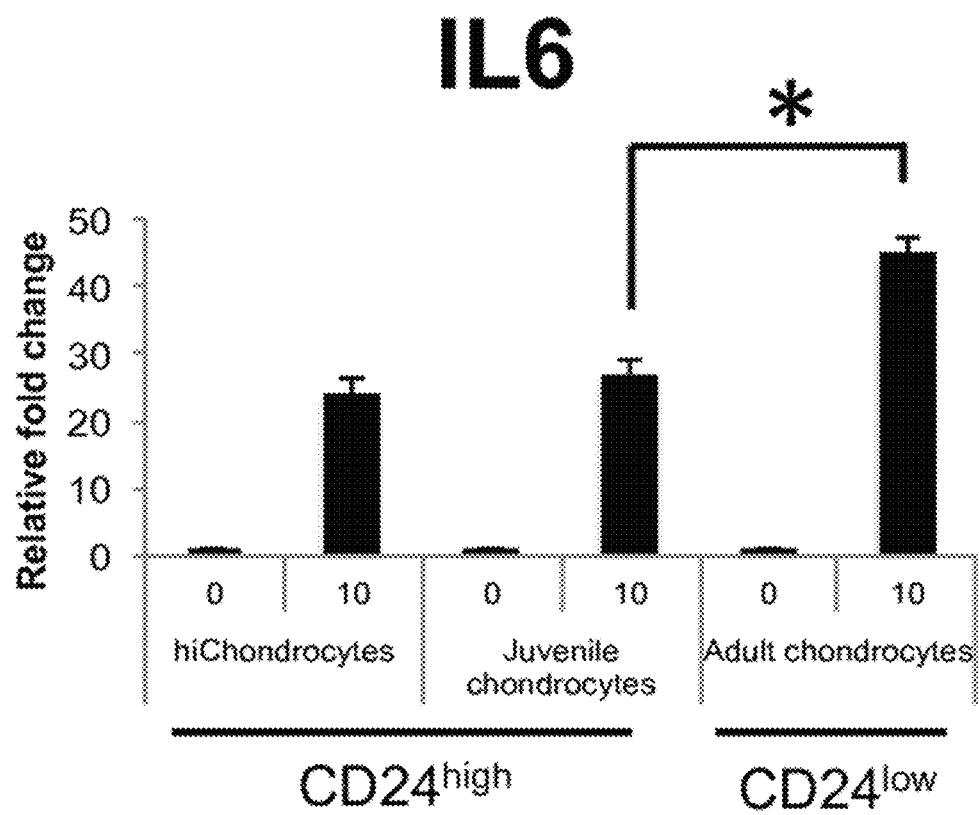
FIGS. 2A-2F show a differential inflammatory response in gene expression of the inflammatory genes, IL6 (FIG. 2A) and CCL2 (FIG. 2B), catabolic genes, MMP3 (FIG. 2C) and ADAMST4 (FIG. 2D), and chondrocyte regulatory genes, COL2A (FIG. 2E) and SOX9 (FIG. 2F), in juvenile (24 weeks), adult (27F) and hiChondrocytes (#16) under IL-1b stimulation (10 ng/ml), (*p<0.01).
Figure 2B:
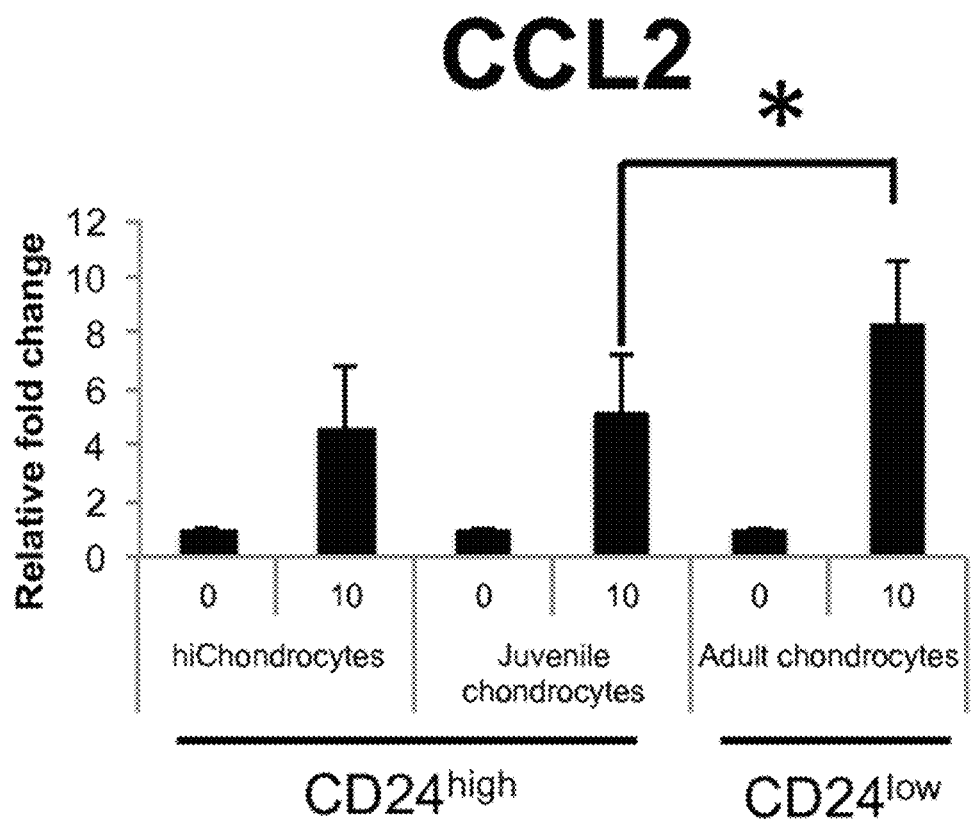
Figure 2C:
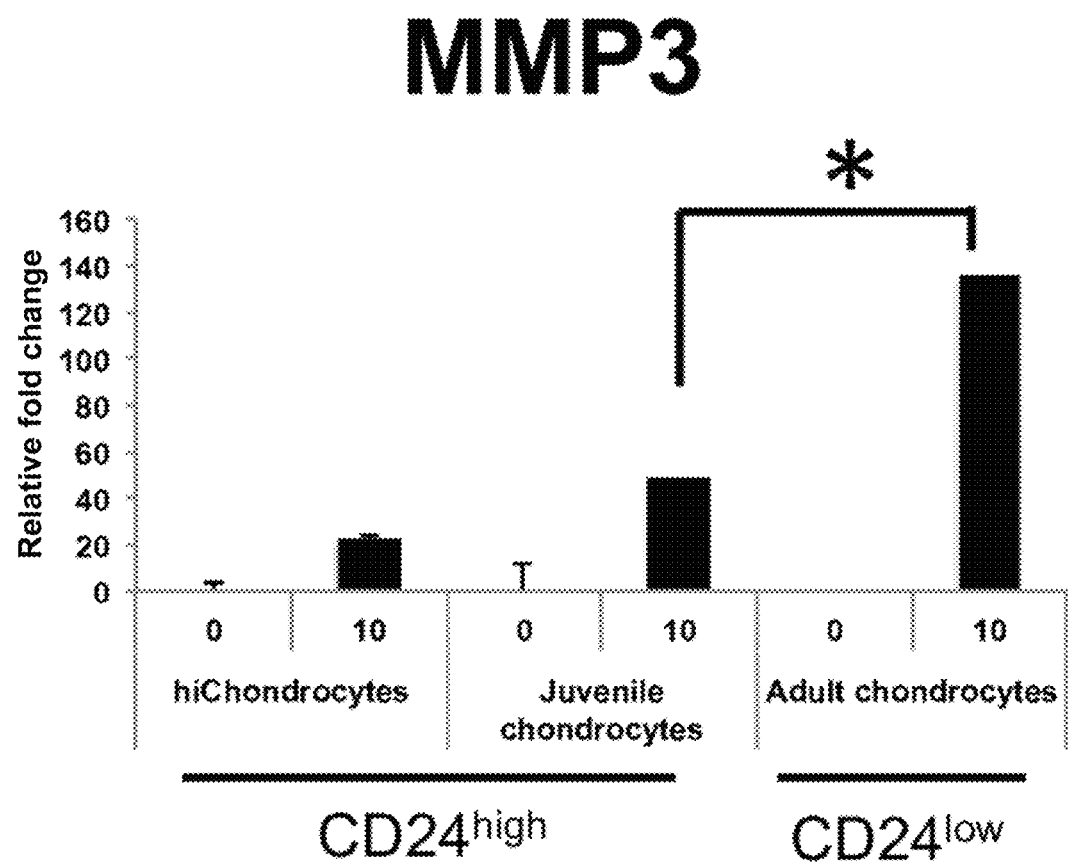
Figure 2D:
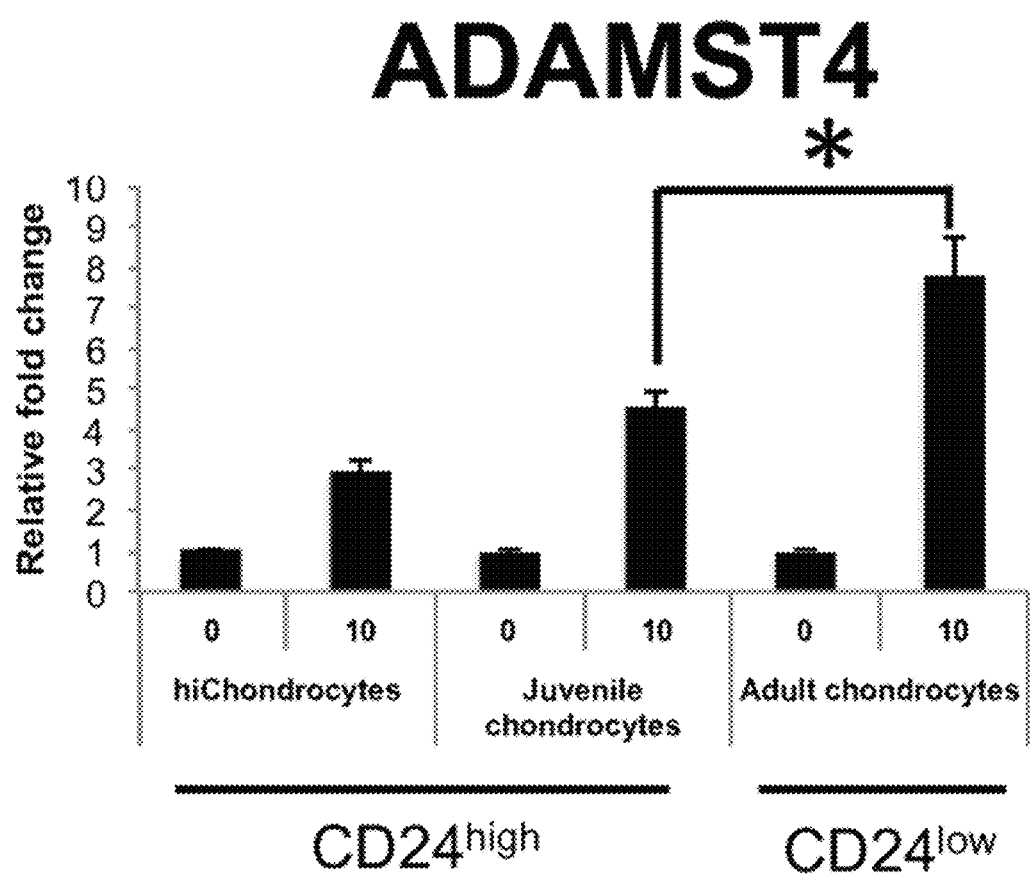
Figure 2E:
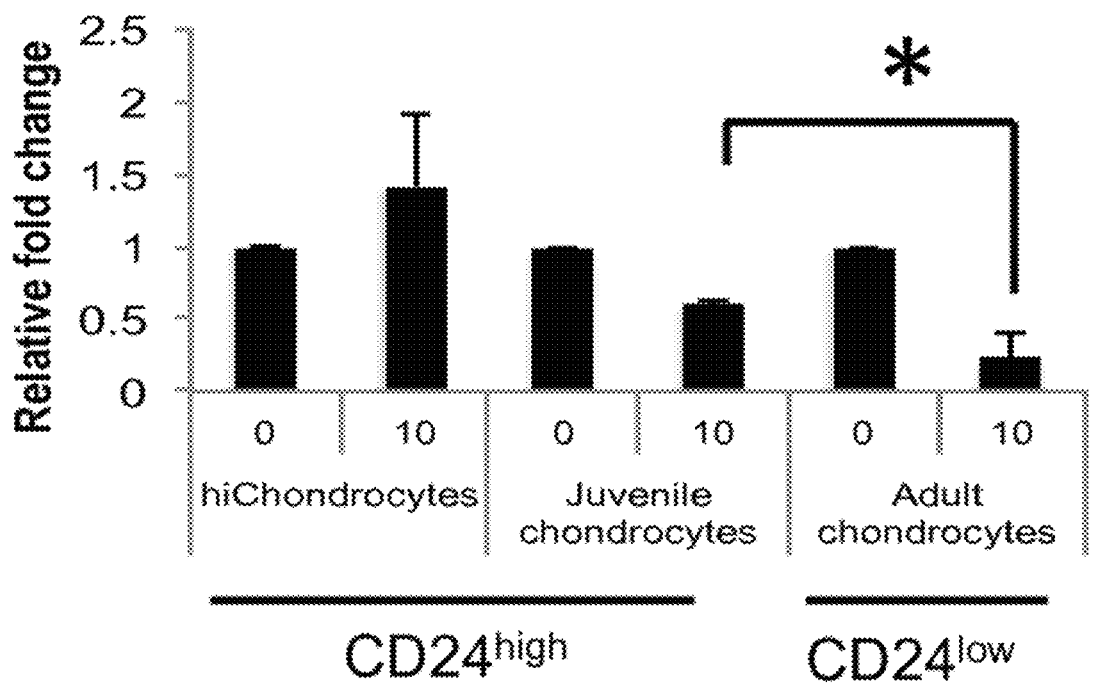
Figure 2F:
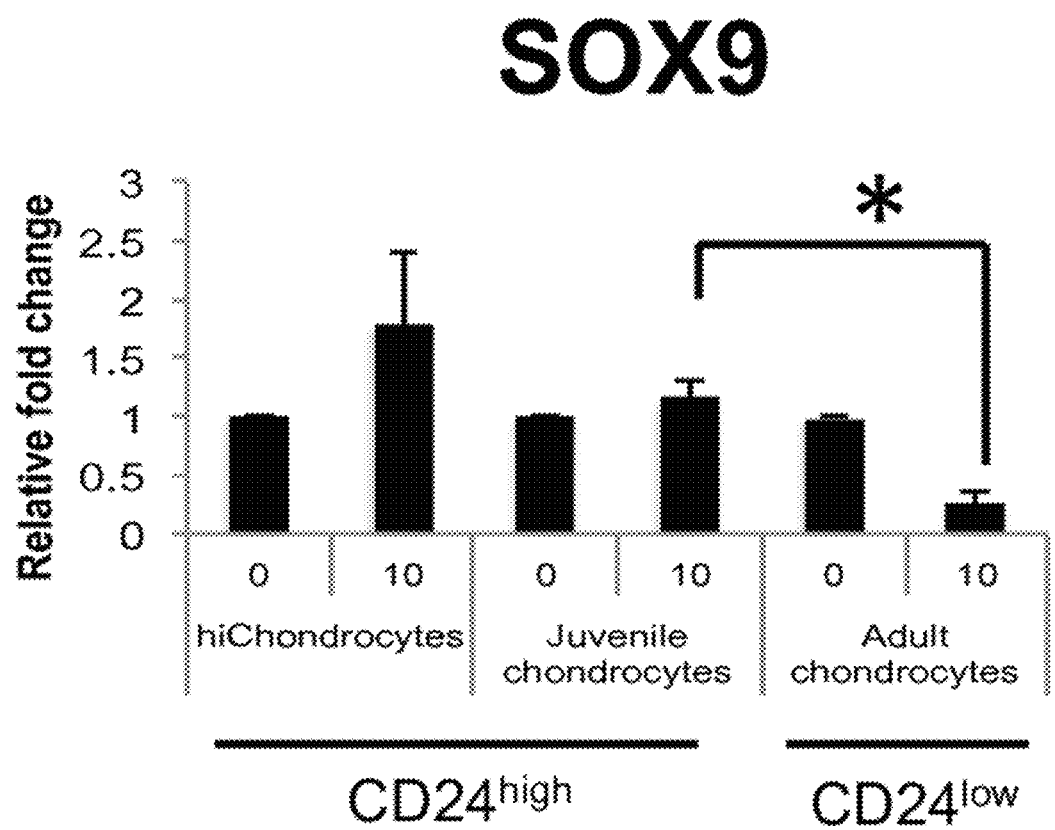

Differential Inflammatory Response in hiChondrocytes, Juvenile and Adult Chondrocytes Since CD24 is known to modulate innate immunity, we tested whether differential expression of CD24 in hiChondrocytes, juvenile and adult chondrocytes will affect the response to pro-inflammatory cues. Since IL-1β plays a major role in inflammation in cartilage, we determined the response to IL-1β treatment in $CD24^{high}$ chondrocytes (hiChondrocytes and juvenile chondrocytes) and $CD24^{low}$ chondrocytes (adult chondrocytes). Upon IL-1β treatment (0 or 10 ng/ml dosage) of chondrocytes for 48 hours, we observed that the expression of inflammatory genes (CCL2 and IL6) was upregulated in all chondrocyte types—hichondrocytes, juvenile and adult chondrocytes (FIG. 2A). However, there was a significantly greater upregulation of both CCL2 and IL6 in the $CD24^{low}$ adult chondrocytes as compared to the $CD24^{high}$ chondrocytes (hiChondrocytes and juvenile chondrocytes) (FIG. 2A). Similarly, upon testing a few catabolic genes, we observed a significantly greater upregulation of MMP3 and ADAMTS4 in the $CD24^{low}$ adult chondrocytes as compared to the $CD24^{high}$ chondrocytes (hiChondrocytes and juvenile chondrocytes) (FIG. 2B). In contrast, chondrogenic gene expression (COL2A1 and SOX9) was significantly decreased only in the $CD24^{low}$ adult chondrocytes in response to IL-1β treatment while the $CD24^{high}$ chondrocytes were resistant and maintained the chondrogenic gene expression (FIG. 2C). Overall, the $CD24^{low}$ chondrocytes showed a greater susceptibility to inflammatory cytokines.

Loss of CD24 Increases Inflammatory Response in Chondrocytes

Figure 3A:
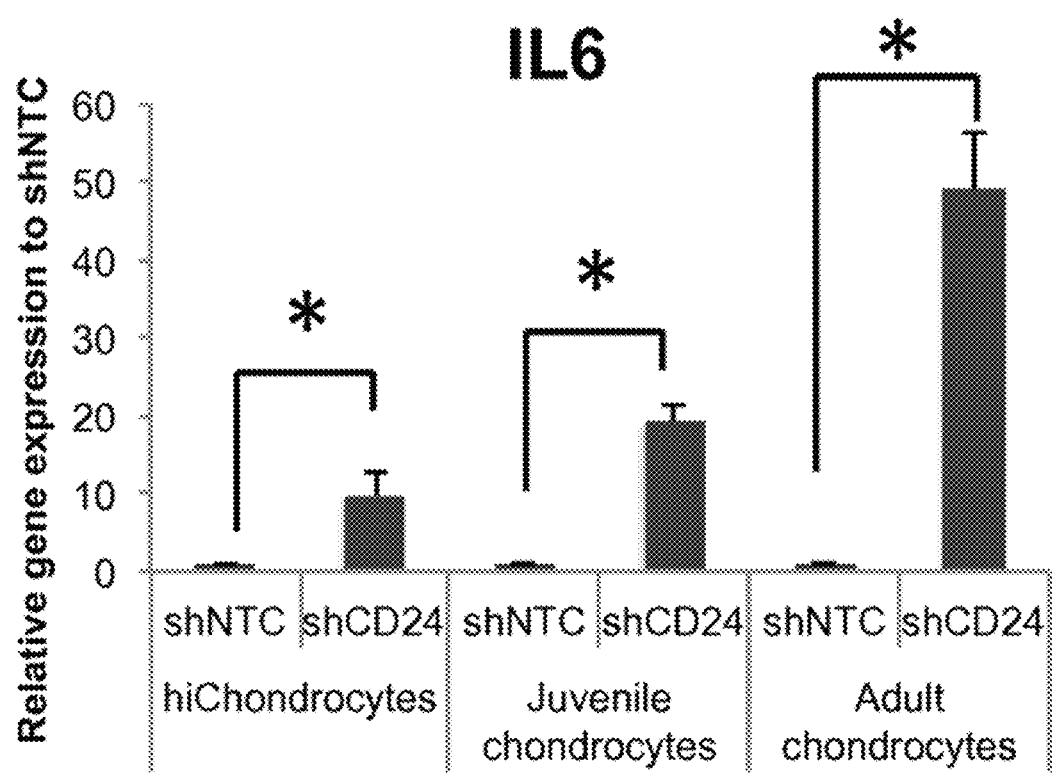
FIGS. 3A-3D show that loss of CD24 in chondrocytes using an shRNA against CD24 increases inflammatory gene expression of IL-6 (FIG. 3A) and CCL2 (FIG. 3B), but not chondrogenic gene expression of COL2A1 (FIG. 3C) or SOX9 (FIG. 3D) in juvenile chondrocytes (24 weeks), adult chondrocytes (27F) and hiChondrocytes (#16), (*p<0.01).
Figure 3B:
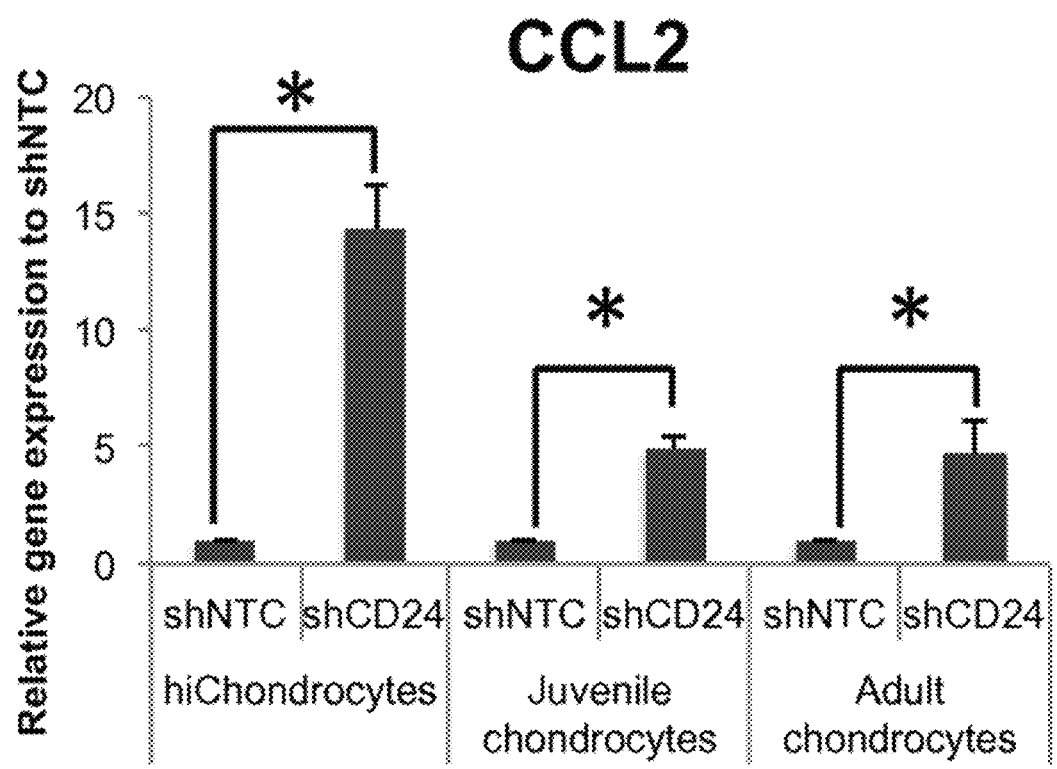
Figure 3C:
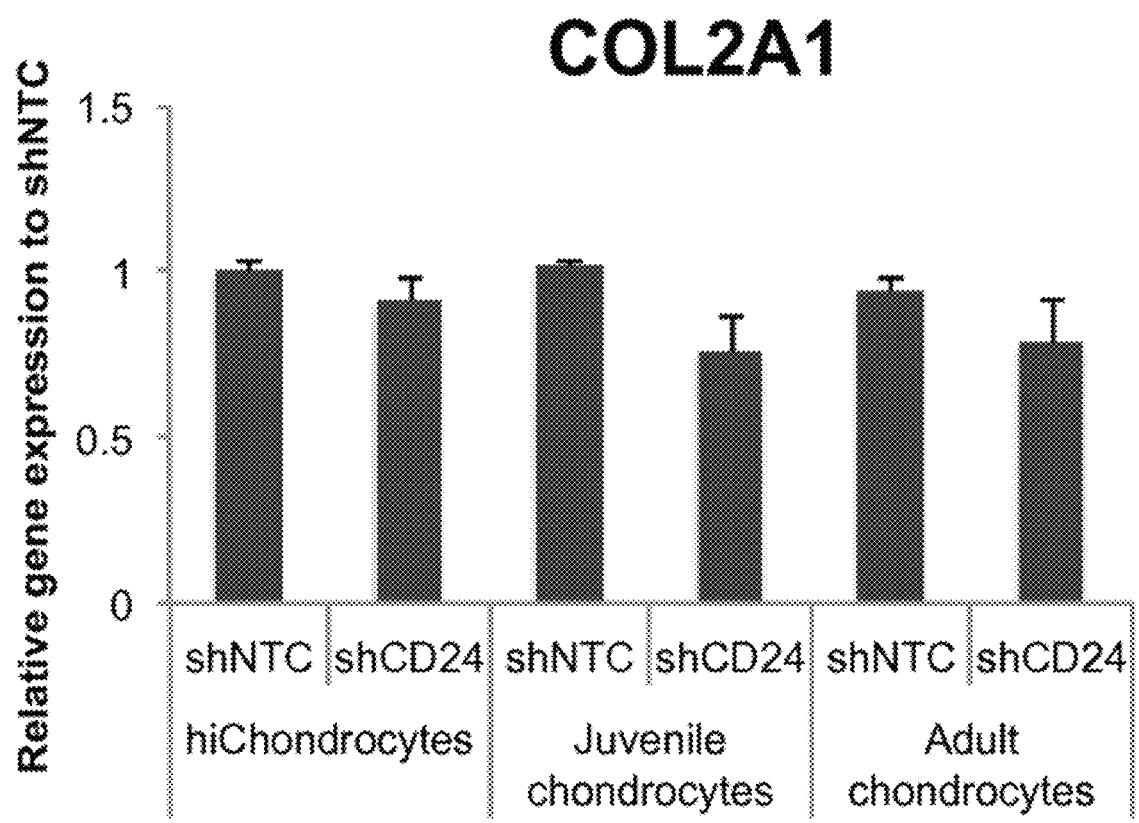
Figure 3D:
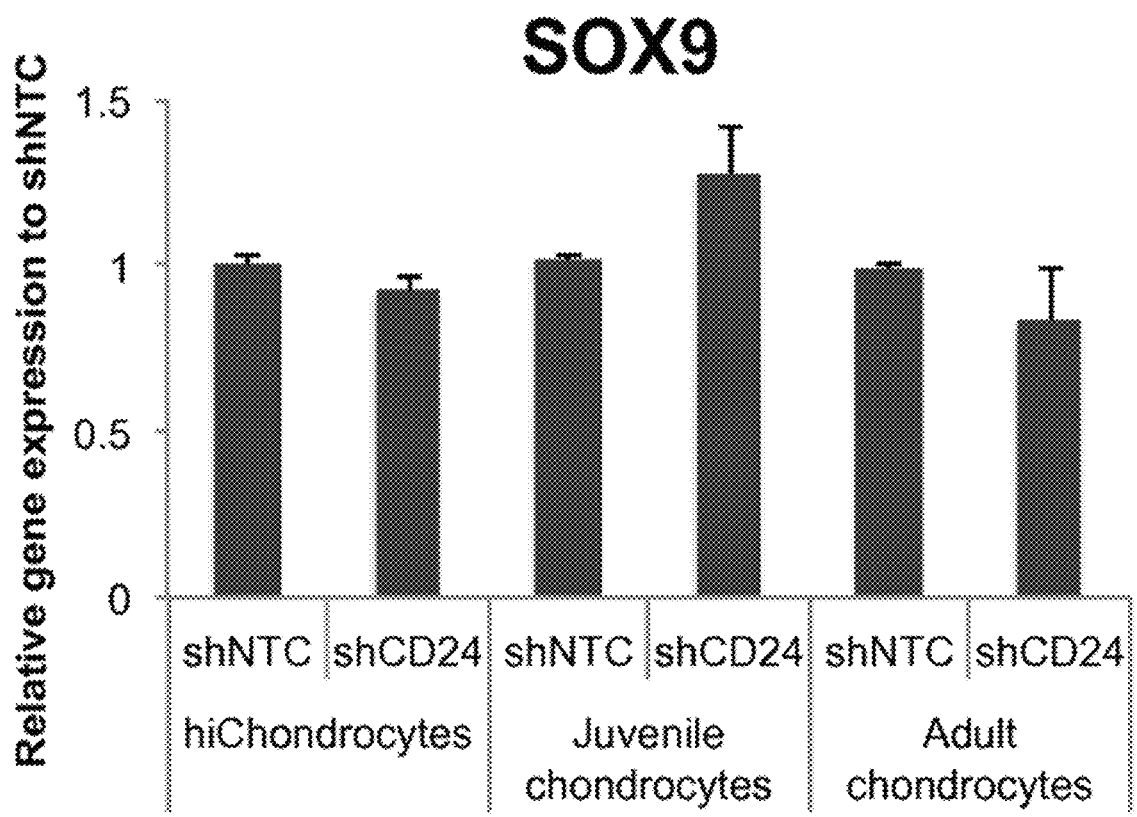
Figure 7A:
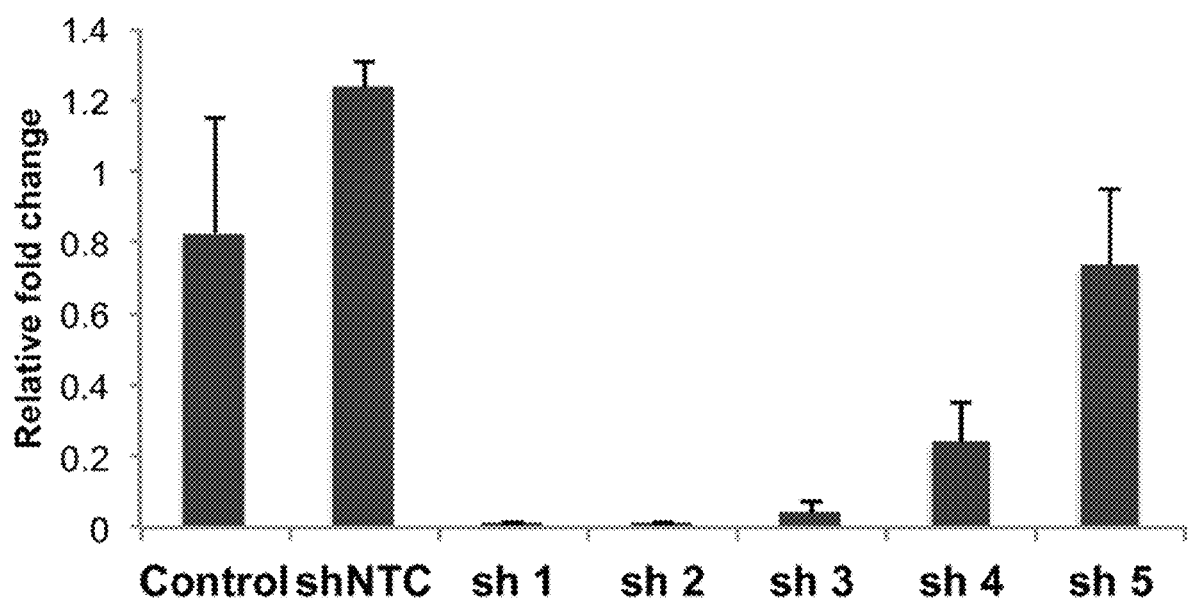
FIGS. 7A-7E show the effects of shCD24 knockdown on chondrocytes.
Figure 7B:
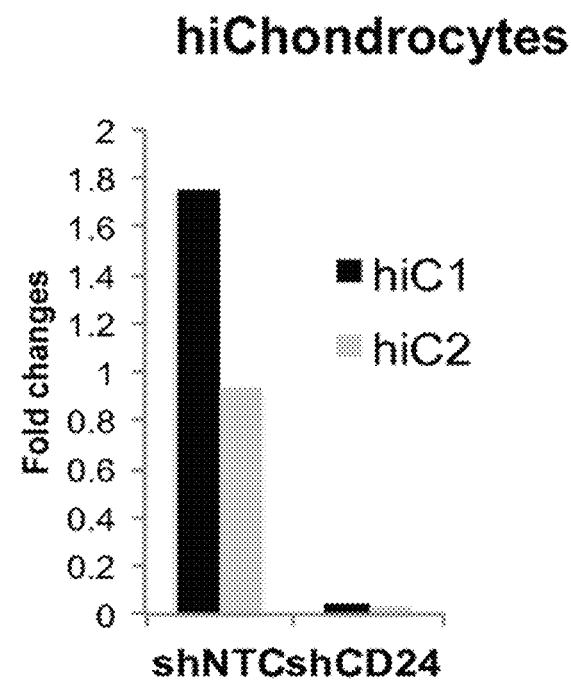
Figure 7C:
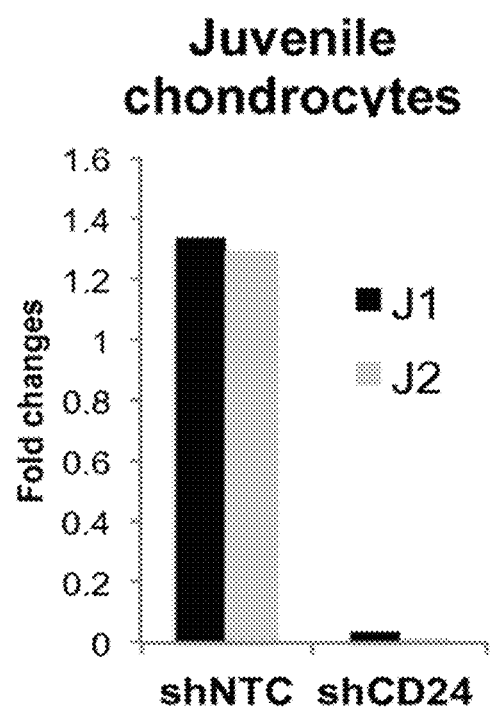
Figure 7D:
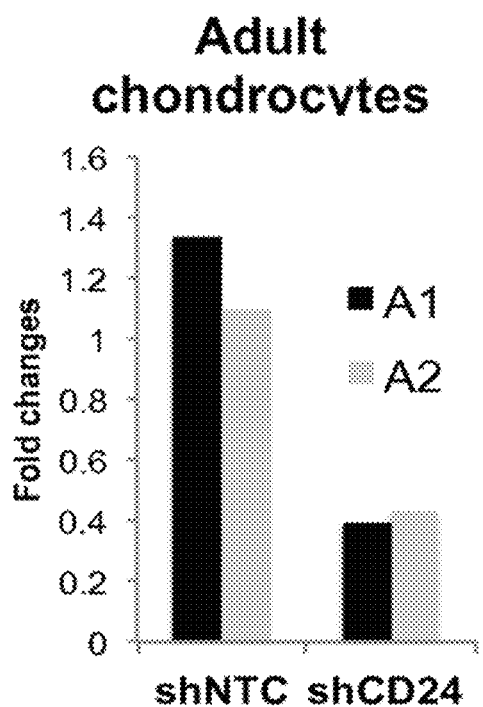
Figure 7E:
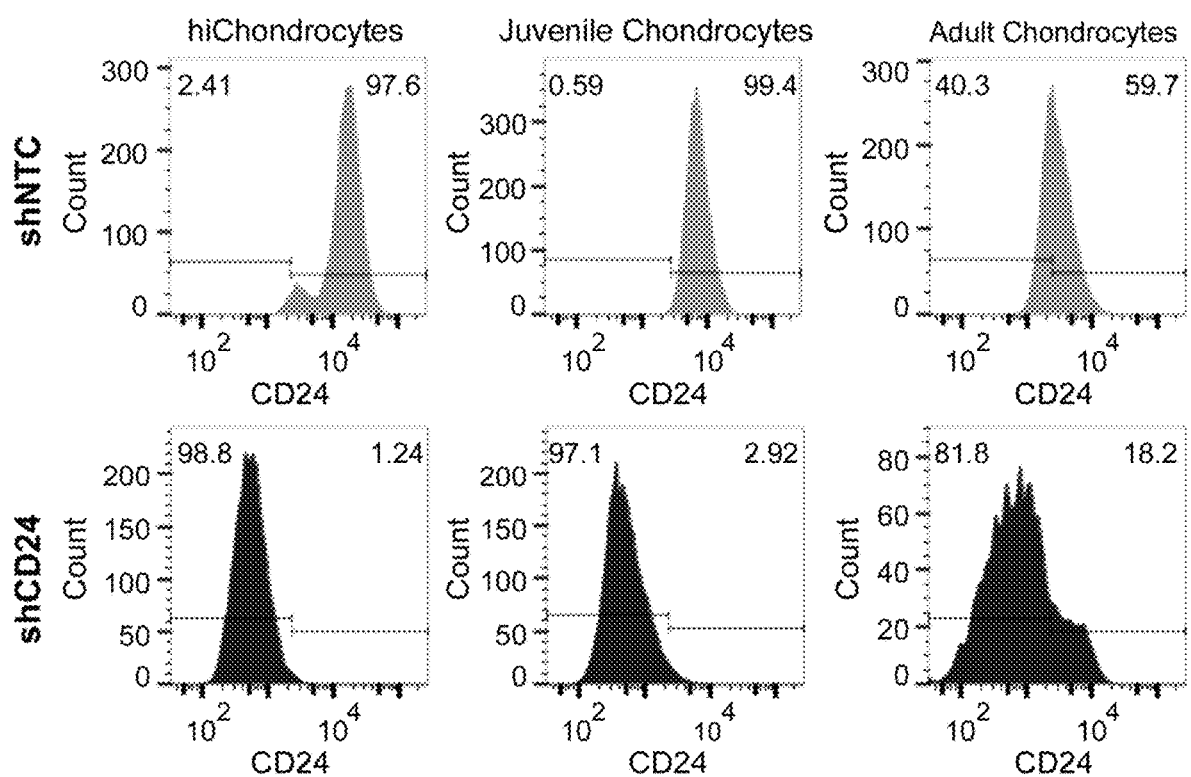
Figure 8A:
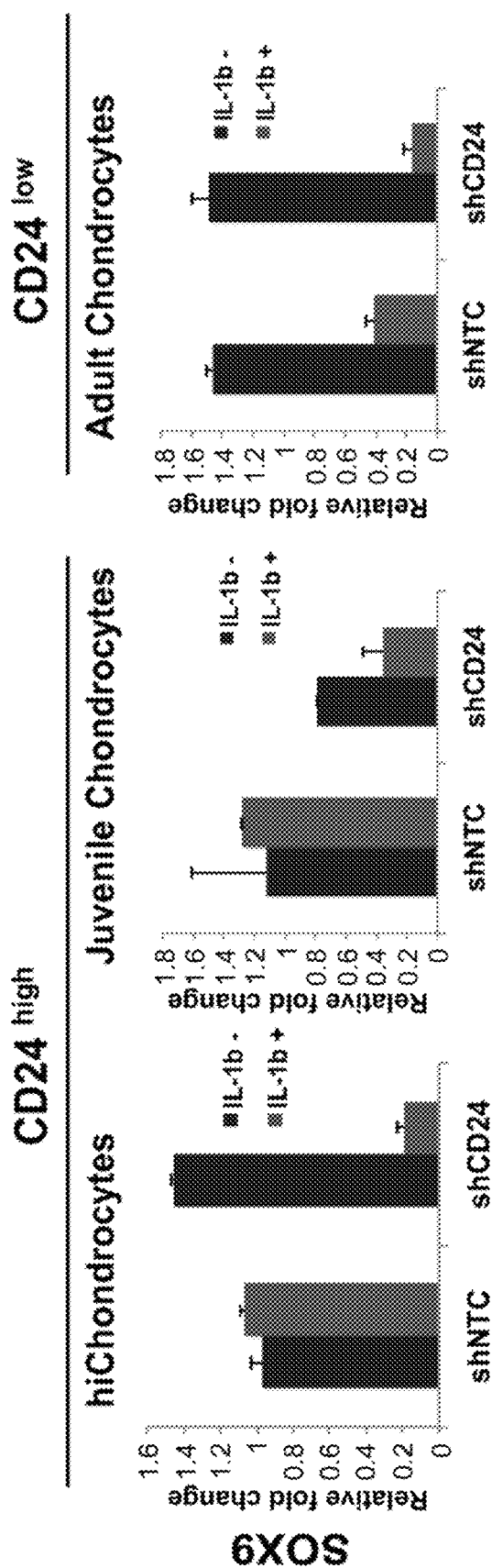
FIGS. 8A and 8B show that loss of CD24 down-regulates the chondrogenic-specific genes, SOX9 (FIG. 8A) and COL2A (FIG. 8B).
Figure 8B:
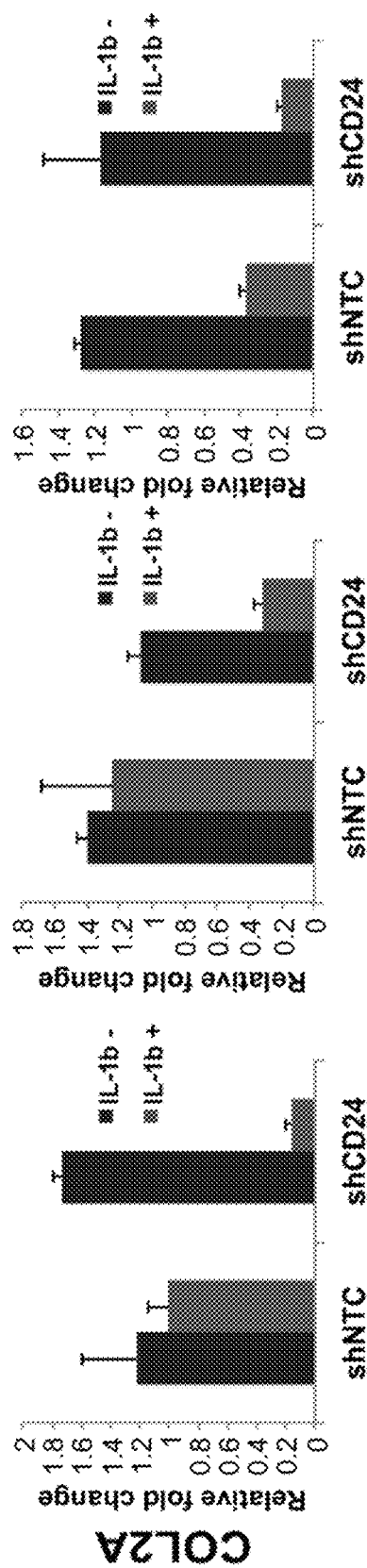
Figure 9A:
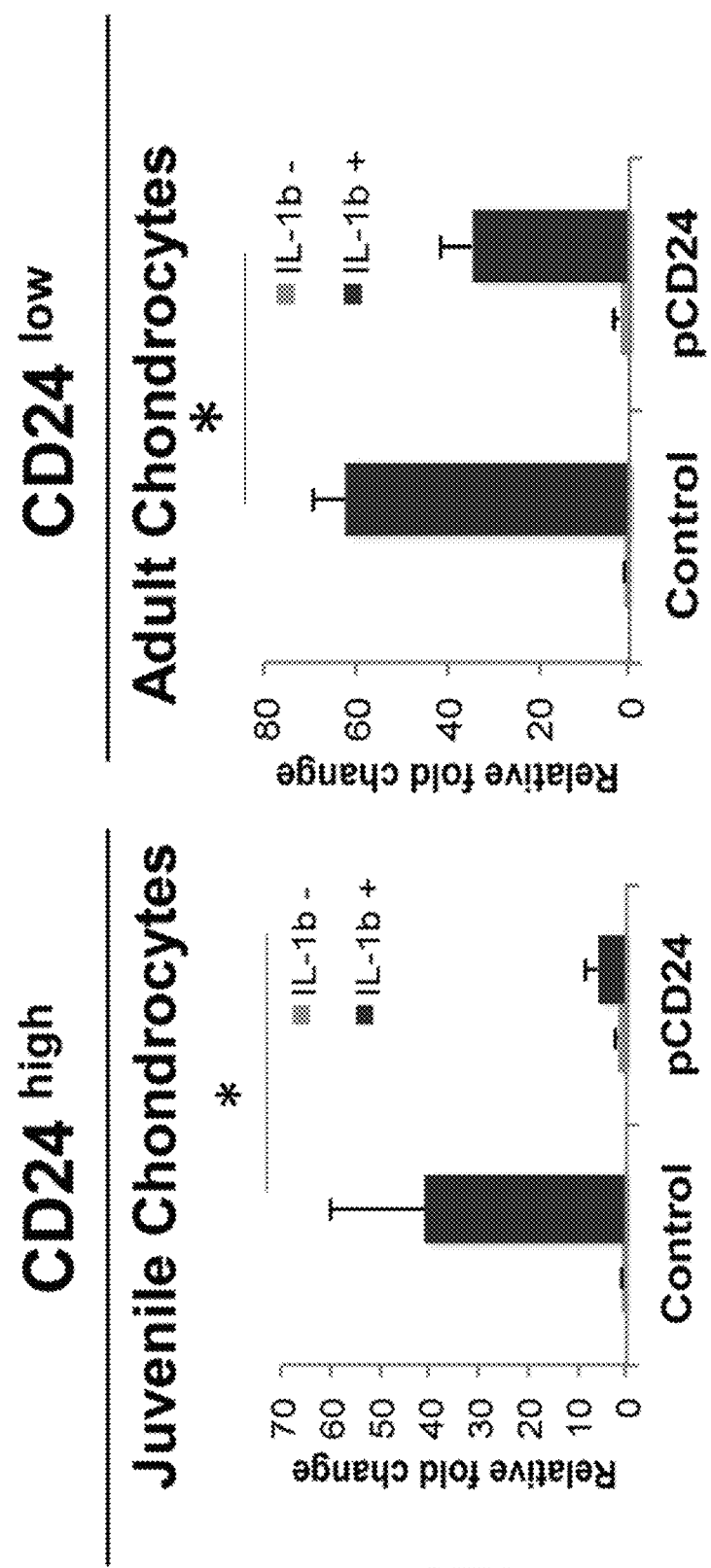
FIGS. 9A-9D show that gain of CD24 reduces the inflammatory response in chondrocytes of IL-6 (FIG. 9A) and CCL2 (FIG. 9B) and decreases catabolic gene expression of MMP3 (FIG. 9C) and ADAMST4 (FIG. 9D) in juvenile chondrocytes (24 weeks), adult chondrocytes (27F) and hiChondrocytes (Batch #16), (*p<0.01).
Figure 9B:
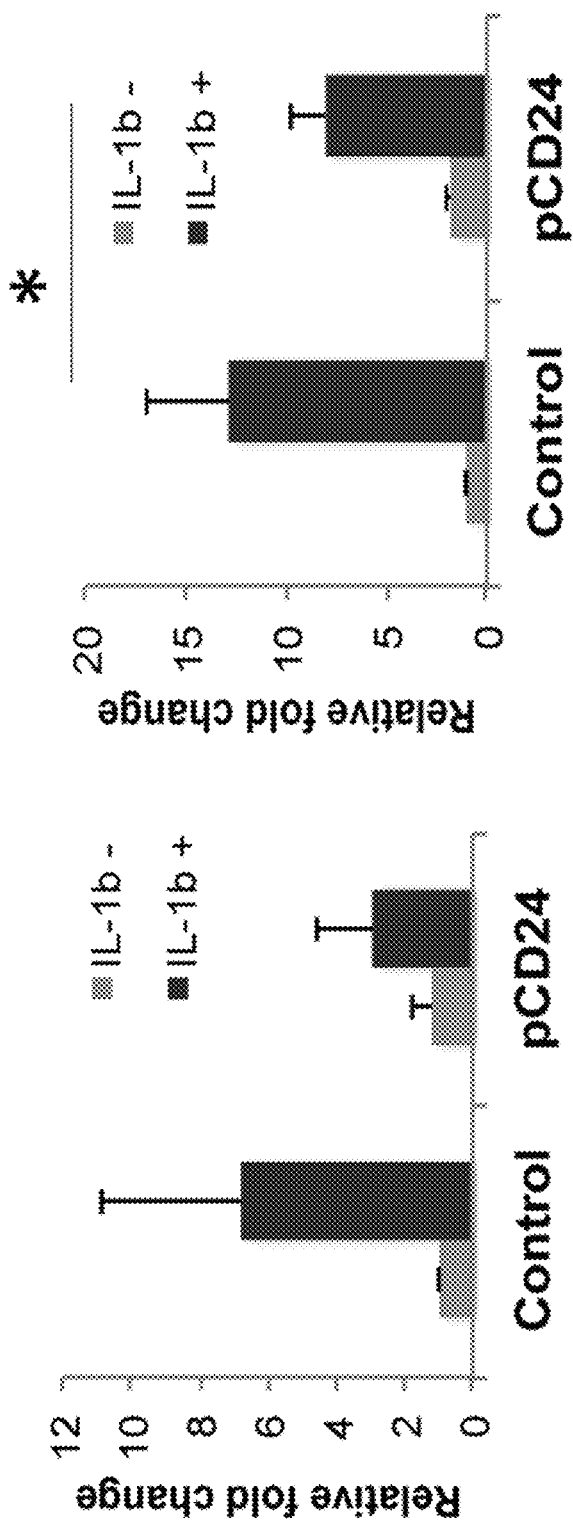
Figure 9C:
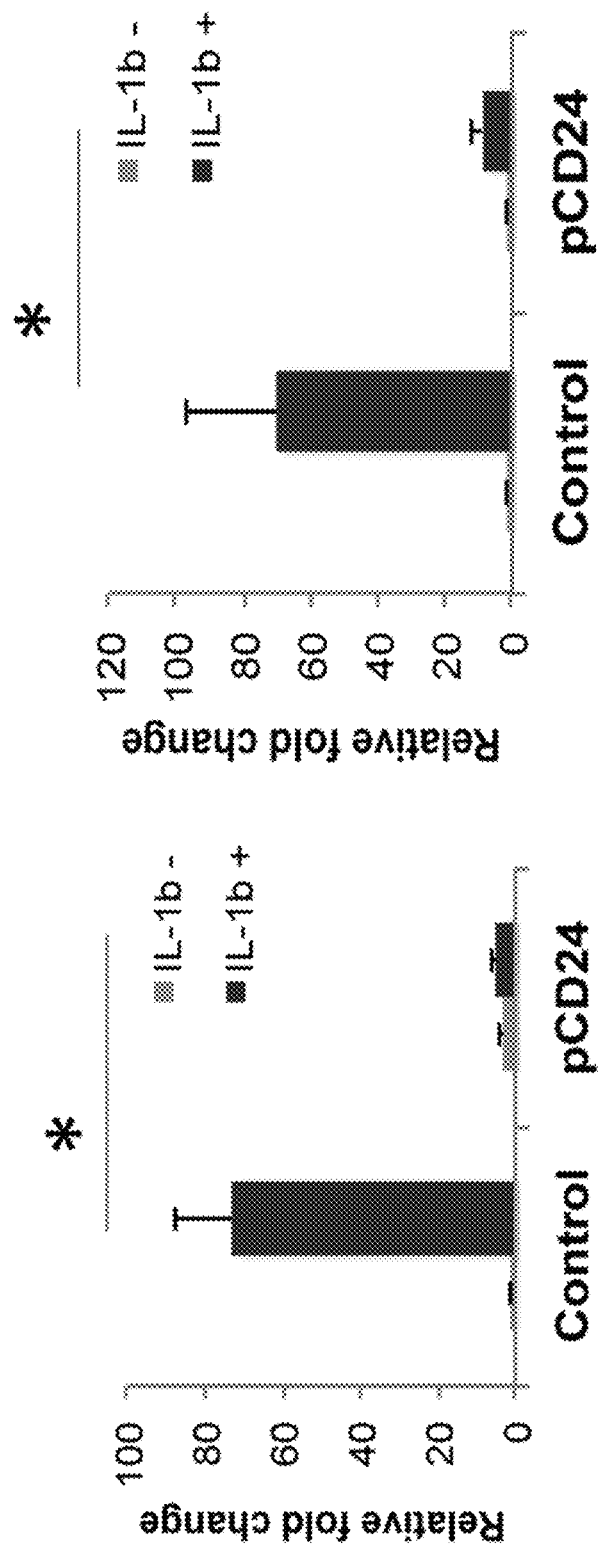
Figure 9D:
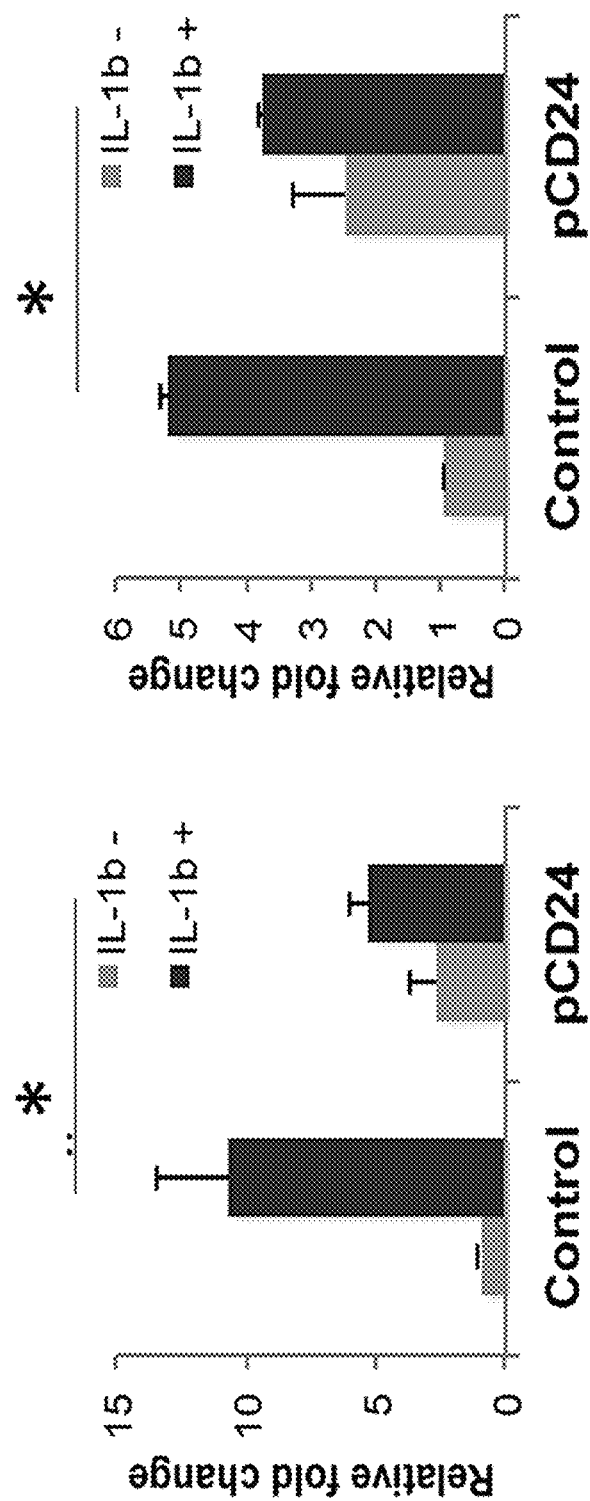
Figure 10A:
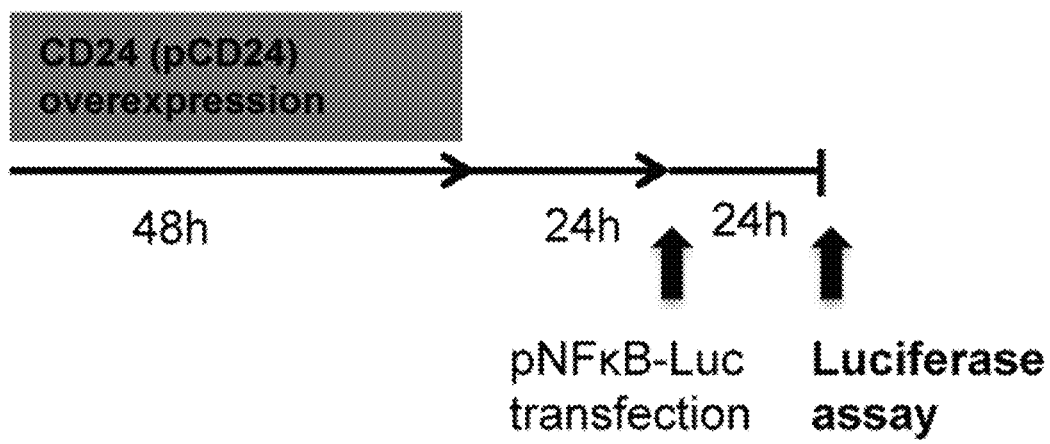
FIGS. 10A and 10B show that CD24 overexpression reduces NF-B activation.
Figure 10B:
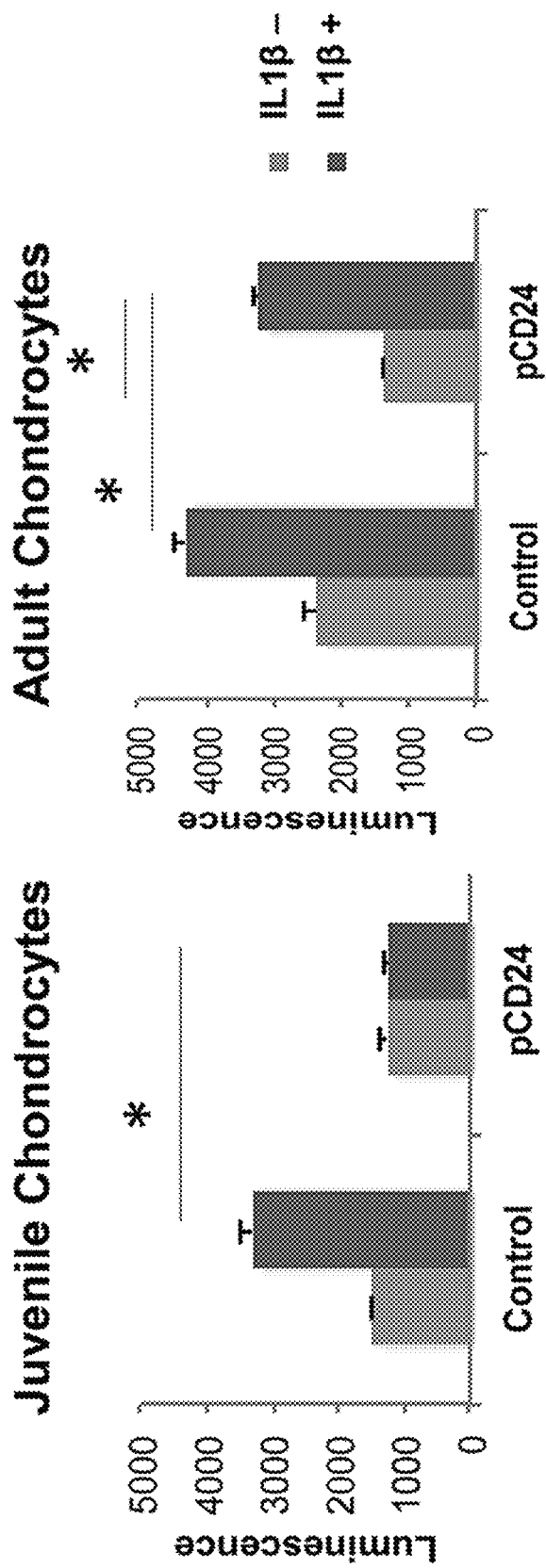

In order to further understand the effect of CD24 expression on the inflammatory and chondrogenic genes, we first investigated the effect of CD24 loss in the hiChondrocytes, juvenile and adult chondrocytes. In order to induce a loss of CD24, we tested a set of five shRNAs and identified three independent shRNAs (sh1, 2 and 3; see methods) that consistently showed an 80% or greater knockdown for CD24 at gene and protein levels (FIGS. 7A-7C). Real-time quantitative PCR was utilized to determine the mRNA levels and single-cell FACS analyses were used to confirm CD24 expression at the protein level. A non-target control shRNA was used along with the CD24 specific shRNA. Upon causing an shRNA-mediated loss of CD24 in chondrocytes, we observed an upregulation of the inflammatory genes IL6 and CCL2 in hichondrocytes, juvenile and adult chondrocytes even in the absence of treatment with any pro-inflammatory cytokines (FIG. 3A). A similar increase was observed in the expression of catabolic genes, MMP3 and ADAMTS4, upon loss of CD24 however this increase was modest and a little variable across the different chondrocytes (FIG. 8). In contrast, loss of CD24 alone (that happens during normal aging) does not alter expression of the chondrogenic genes, Col2a1 and Sox9 (FIG. 3B).

Figure 4A:
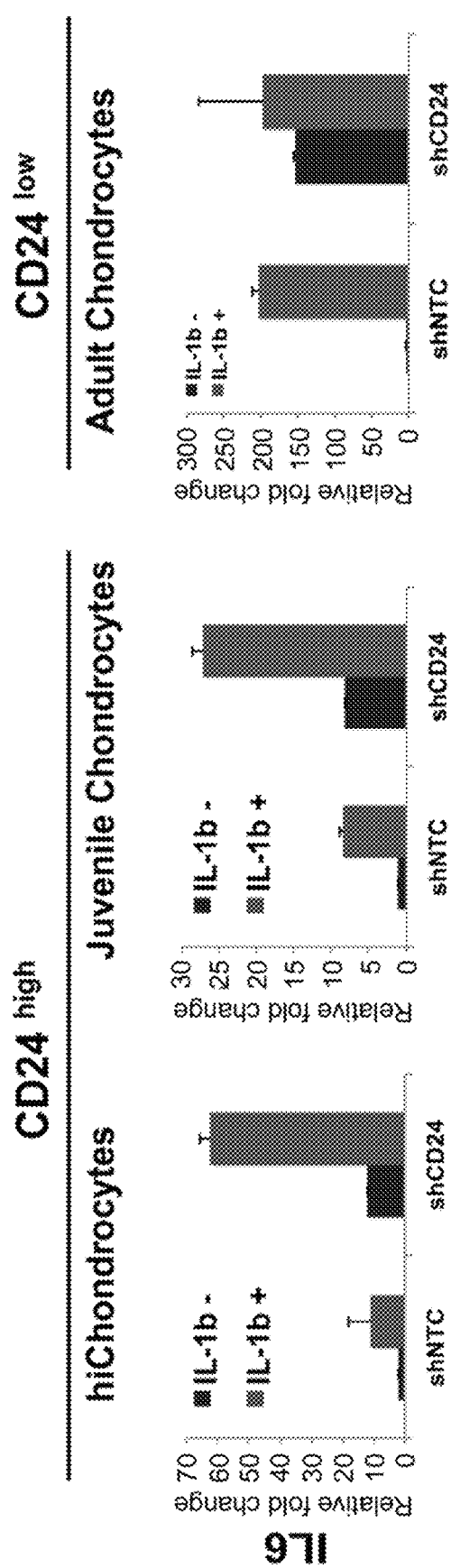
FIGS. 4A-4D show that loss of CD24 enhances the inflammatory response of IL6 (FIG. 4A) and CCL2 (FIG. 4B) and increases expression of catabolic genes MMP3 (FIG. 4C) and ADAMST4 (FIG. 4D) in juvenile chondrocytes (24 weeks), adult chondrocytes (27F) and hiChondrocytes (Batch #16).
Figure 4B:
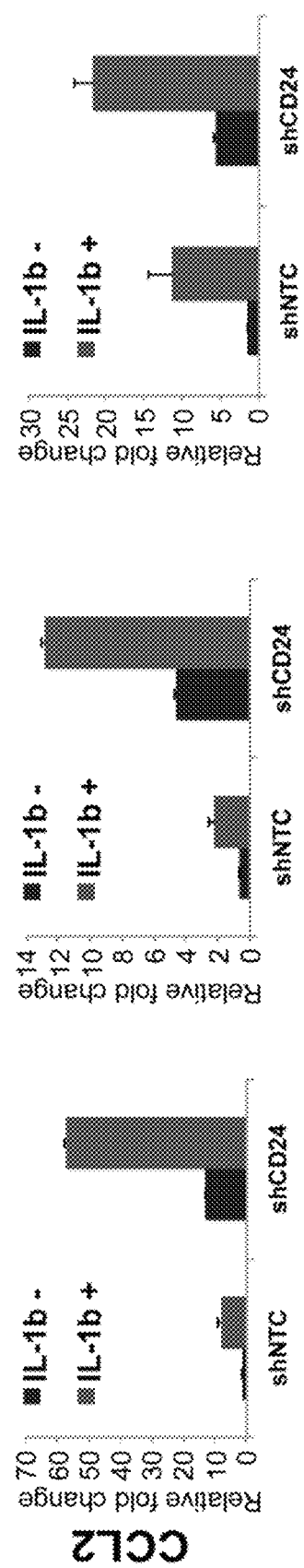
Figure 4C:
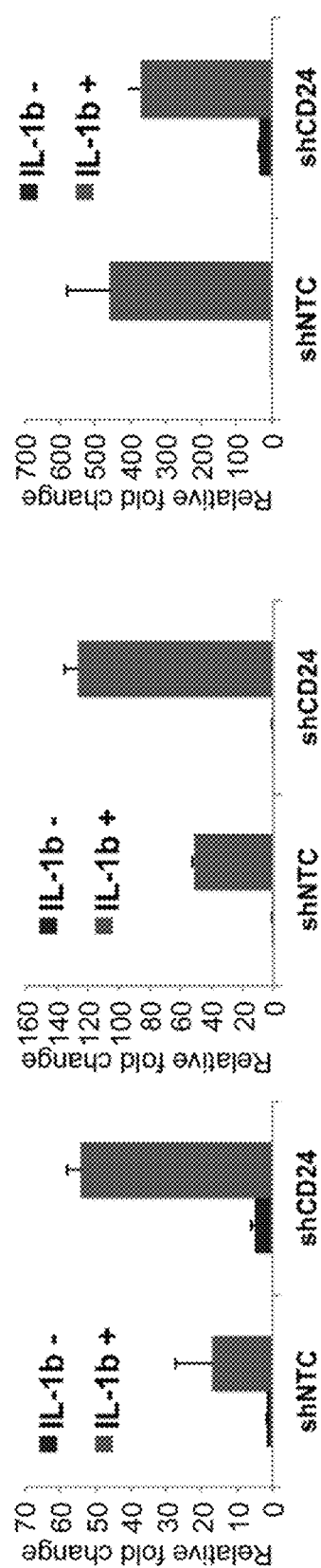
Figure 4D:
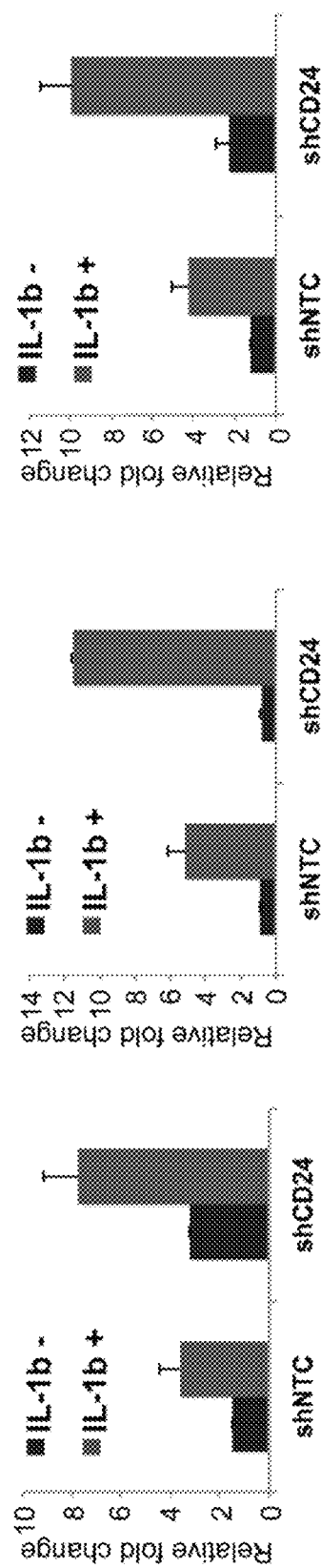

Next, we assessed the effect of loss of CD24 in chondrocytes upon exposure to pro-inflammatory cytokines. Chondrocytes transduced with either the non-target control or CD24-specific shRNA were treated with IL-1β treatment (0 or 10 ng/ml dosage) for 48 hours. Gene expression of inflammatory (IL6 and CCL2), catabolic (MMP3 and ADAMTS4) and chondrogenic (Col2a1 and Sox9) genes were then assayed using quantitative PCR. Loss of CD24 acted synergistically with IL-1β treatment showing a significantly higher upregulation of IL6, CCL2, MMP3 as well as ADAMTS4 in hichondrocytes and juvenile chondrocytes (FIGS. 4A, 4B). For adult chondrocytes that already had a small subset of cells expressing CD24, loss of CD24 further increased upregulation of CCL2 and ADAMTS4 significantly but not of IL6 or MMP3 (FIGS. 4A, 4B). Interestingly, loss of CD24 rendered the hichondrocytes and juvenile chondrocytes susceptible to dedifferentiation in the presence of IL-1β while these chondrocytes were protected from the IL-1β-mediated loss of Col2a1 and Sox9 in the presence of CD24.

CD24 Inhibits NFκB Activation in Chondrocytes

Figure 5A:
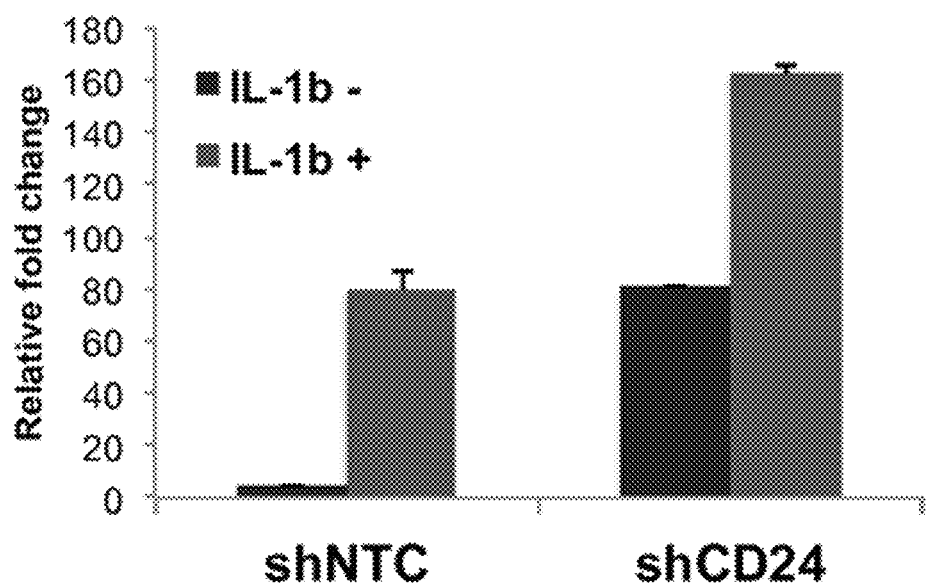
FIGS. 5A-5G show that CD24 negatively mediates NFκB signaling to activate an inflammatory response.
Figure 5B:
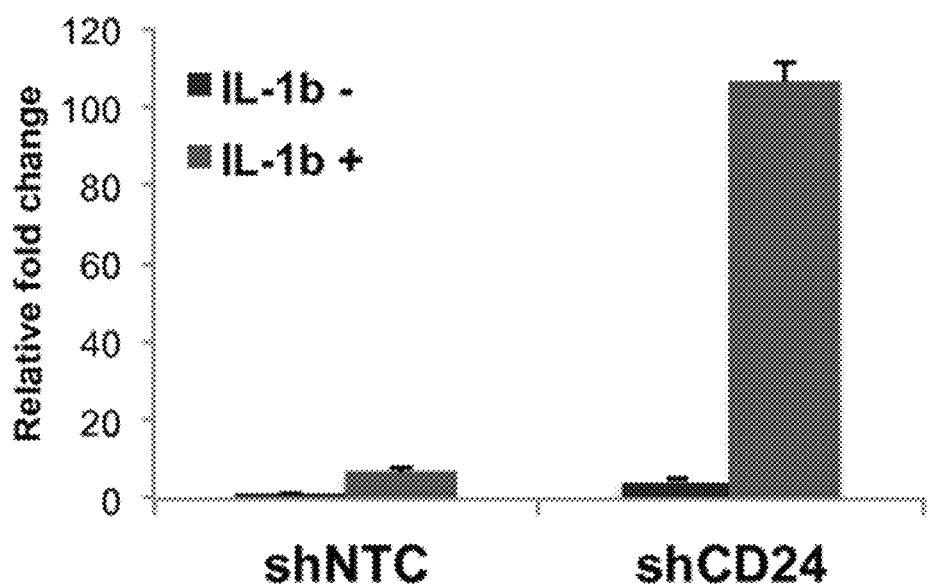
Figure 5C:
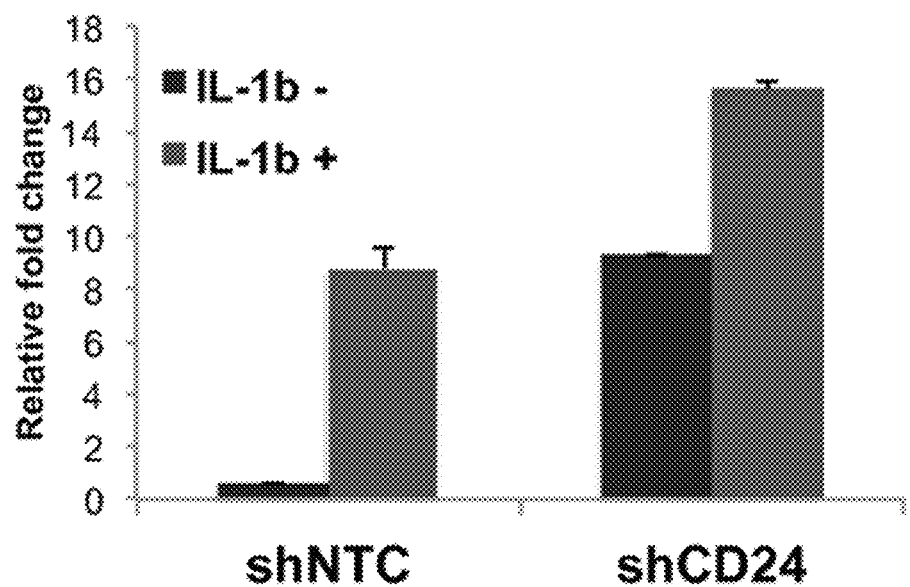
Figure 5D:
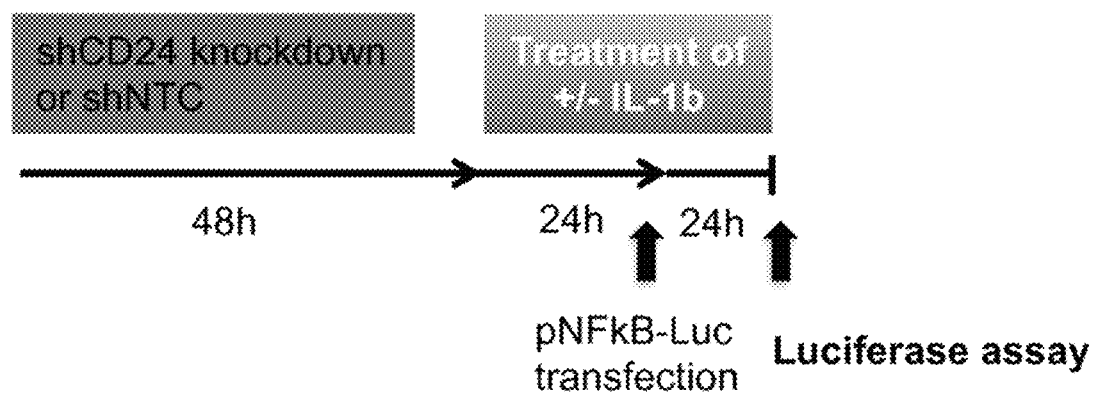
Figure 5E:
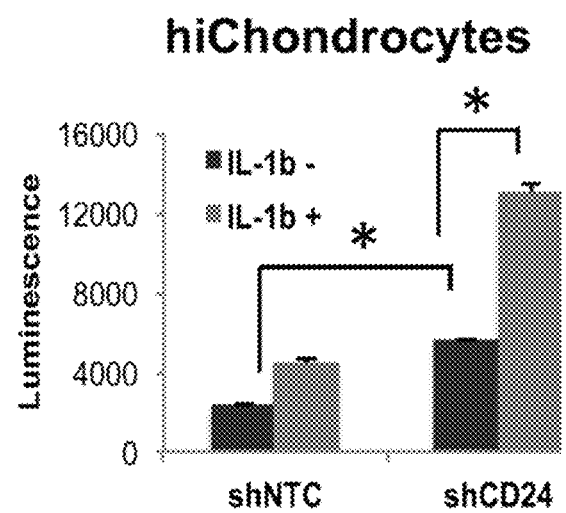
Figure 5F:
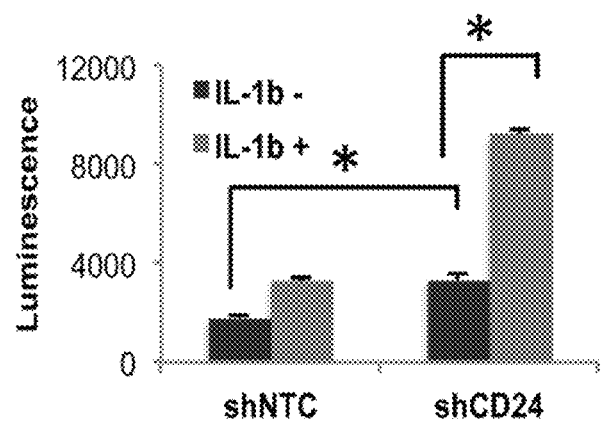
Figure 5G:
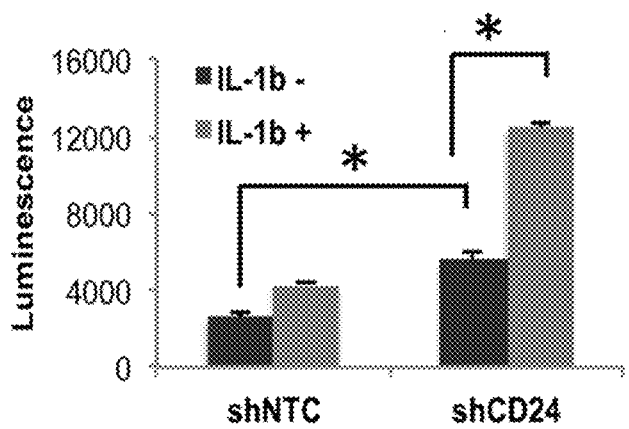
Figure 6A:
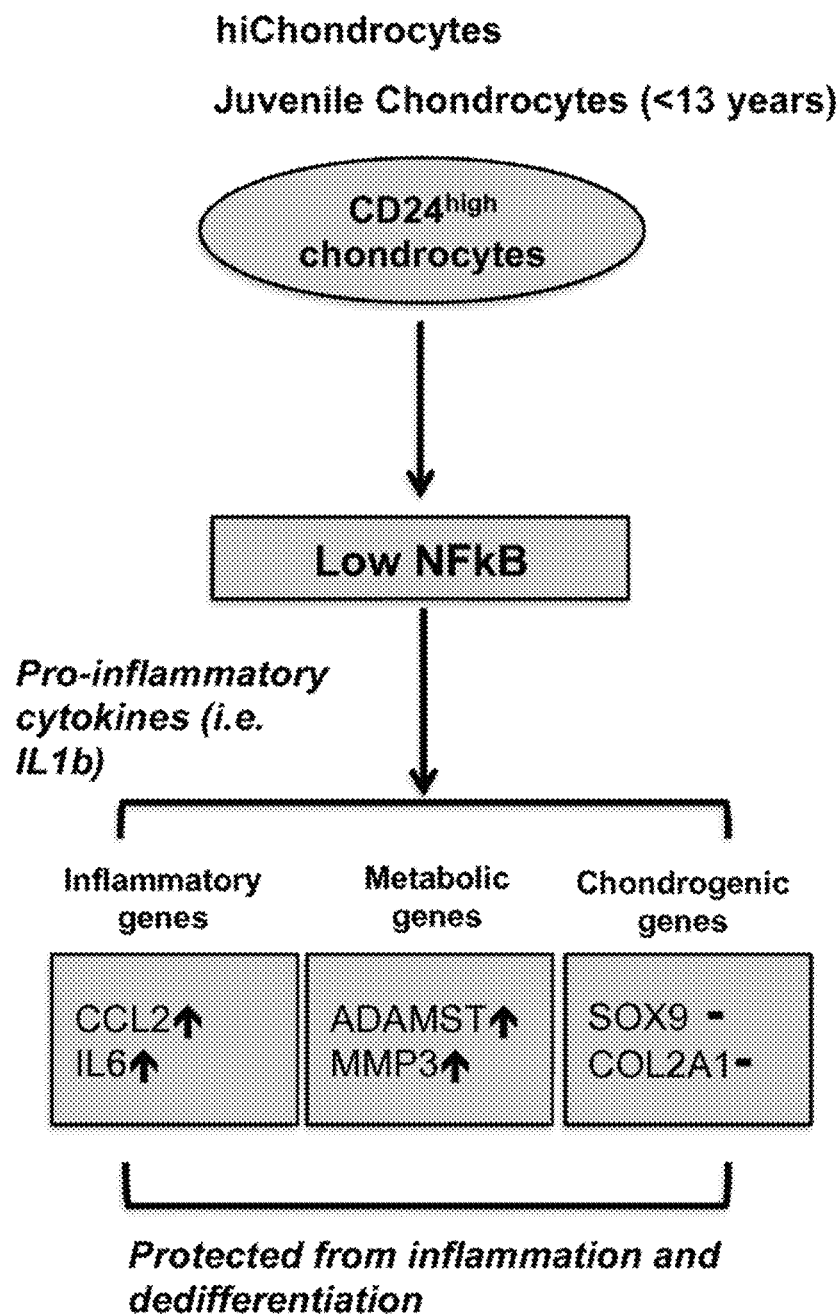
FIGS. 6A and 6B show a schematic review of differences between CD24$^{high}$ chondrocytes (FIG. 6A) and CD24$^{low}$ chondrocytes (FIG. 6B).
Figure 6B:
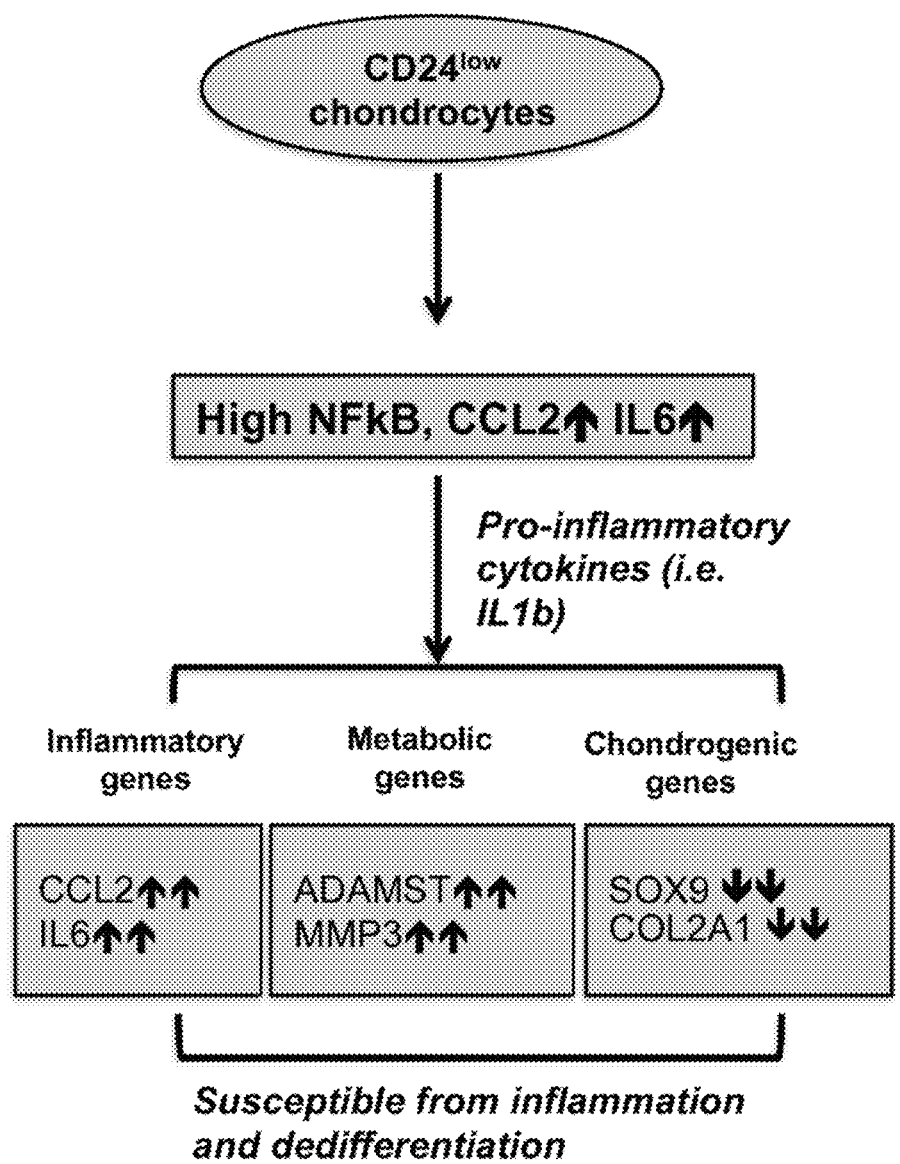

Nuclear factor-kappaB (NFκB) pathway is known to regulate expression of inflammatory and catabolic genes in osteoarthritis (OA). Previous studies have shown that CD24 signaling can modulate NFκB activity in immune cells; therefore, we tested whether CD24 expression modulates NFκB activity in chondrocytes as well. We have therefore examined both NFκB gene expression and activity in the absence and presence of CD24. Loss of CD24 by itself significantly increased NFκB gene expression in hichondrocytes, juvenile and adult chondrocytes (FIG. 5A). NFκB activity was investigated using a NFκB reporter luciferase assay, as described previously (FIG. 5B). Chondrocytes transduced with control or CD24 shRNA, were treated with IL-1β treatment (0 or 10 ng/ml dosage) for 48 hours. After 24 hours of treatment, the NFκB-responsive luciferase construct was transfected in the chondrocytes, and assayed after another 24 hours (Schematic, FIG. 5B). A significant increase in relative luminescence, representing luciferase activity, was observed upon loss of CD24 that increased synergistically upon IL-1β treatment in all chondrocytes (FIG. 5B).

Discussion

Juvenile chondrocytes (from donors less than 13 years of age) have emerged in recent years as an attractive cell source for cartilage regeneration and tissue engineering. Demonstrated differences between the juvenile and adult chondrocytes include increased proliferation and ECM generation in juvenile chondrocytes. In addition, transplantation of allogeneic juvenile chondrocytes without any adverse effects and their inability to stimulate immune cells has suggested that they are immune-privileged. In the present studies, we have additionally characterized human induced pluripotent stem cells (hiPSC)—derived chondrocytes (hiChondrocytes) that are a model for embryonic neonatal chondrocytes. In studying hiChondrocytes (neonatal), juvenile chondrocytes (<13 years old donors) and adult chondrocytes (25-27 years old donors), we are able to study a spectrum of early human cartilage development and aging especially the response of these chondrocyte subsets to inflammatory cues. Interestingly, our studies demonstrate that hiChondrocytes, juvenile chondrocytes and adult chondrocytes show a differential response to pro-inflammatory cues exemplified by IL-1β. Upon IL-1β stimulation, there was a greater upregulation of both inflammatory (like CCL2 and IL6) and catabolic (MMP3 and ADAMTS4) genes in adult chondrocytes compared to both hiChondrocytes and juvenile chondrocytes, revealing that the adult chondrocytes show a greater susceptibility to inflammatory cues. In addition, the adult chondrocytes are also more prone to dedifferentiation than the younger chondrocytes since they showed a rapid loss of expression of chondrogenic genes, Sox9 and Col2a1, in the presence of IL-1β. These results indicate that the neonatal and juvenile chondrocytes are protected against inflammation and that this protection is gradually lost with aging. In further studies, we would like to extend this characterization to chondrocytes from donors 40-60 years of age to discern whether the responsiveness to inflammatory cytokines is increased further with aging.

A central revelation of our studies is that CD24 is a novel molecular factor enriched in hiChondrocytes and juvenile chondrocytes that regulates response towards inflammatory cues. CD24 is a small, heavily glycosylated and glycosyl phosphatidylinositol (GPI)-anchored cell-surface protein that is a co-stimulator for antigen-specific T cell responses and a differentiation marker for B cells (Taguchi et al. (2003) J. Immunol. 170(1):252-260; Li et al. (2004) J. Exp. Med. 200(8):1083-1089). Importantly, polymorphisms of human CD24 are associated with risk and progression of several autoimmune diseases, multiple sclerosis and rheumatoid arthritis (RA) (Rueda et al. (2008) J Rheumatol. 35(5):850-4; Sanchez et al. (2007) Arthritis Rheum. 56(9):3080-3086; Wang et al. (2007) PLoS Genet 3(4):e49; Zhou et al. (2003) Proc. Natl. Acad. Sci. USA 100(25):15041-15046). In addition, CD24 expression and its prognostic significance has been reported for many types of cancer including breast, colorectal, gastric, lung ovarian, pancreatic cancers, supporting the CD24 as a cancer diagnostic marker (Kristiansen et al. (2004) J. Mol. Histol. 35(3):255-262, Baumann et al. (2005) Cancer Res. 65(23):10783-10793, Kristiansen et al. (2010) Lab Invest. 90(7):1102-1116, Darwish et al. (2004) Cancer Res. Treat. 36(5):298-302). While the function of CD24 in immune cells has been in focus in autoimmune diseases and RA, our studies provide the important insight that changes in CD24 expression in cartilage additionally modulate the cartilage response towards inflammation and hence contribute to RA pathology.

Although the clinical significance and function of CD24 in various diseases have been frequently reported, the regulatory and signaling mechanisms of CD24 are only beginning to be understood. CD24 does not contain a cytosolic domain; hence, it needs to associate with and signal through another cell-surface receptor. In innate immune cells, CD24 has been shown to associate with Siglec-G, a member of the sialic acid-binding immunoglobulin-like lectin family in response to endogenous damage signals like high mobility group box 1 (HMGB1), heat shock protein 70 (HSP70) and heat shock protein 90 (HSP90) that are a part of the damage associated molecular patterns (DAMP). Siglec-G contains cytosolic domains that inhibit NFκB such that a loss of CD24 or Siglec-G can aberrantly activate NFκB. Both CD24- and Siglec-G deficient mice, although viable, have been reported to demonstrate an intense response to induced inflammation in liver leading to acute and lethal liver damage. Blocking CD24 through soluble CD24, consisting of the extracellular portion of murine CD24 and human IgG1 Fc ameliorated the clinical symptom of experimental autoimmune disease, the mouse model of multiple sclerosis (Bai et al. (2000) J. Clin. Invest. 105(9):1227-1232).

In the present studies, we demonstrate that the presence of high CD24 in the $CD24^{high}$ hiChondrocyte and juvenile chondrocyte populations keeps NFκB activation in check while a higher NFκB activity is observed in $CD24^{low}$ adult chondrocytes. The higher NFκB activity in adult chondrocytes is accompanied by a higher baseline expression of CCL2 and IL6, and upon cytokine stimulation leads to a synergistically higher upregulation of inflammatory and catabolic genes along with a rapid downregulation of chondrogenic genes. Therefore, we have identified CD24 to be a novel modulator of the downstream NFκB pathway in chondrocytes. In future studies, we will explore the cartilage-specific CD24 cofactors that signal the inhibition of NFκB (the Siglec family for example).

Decrease of CD24 expression in chondrocytes with aging may be a contributory factor in the early onset and progression of cartilage degenerative diseases especially rheumatoid arthritis. Although osteoarthritis has been classically considered as a non-inflammatory cartilage disease, recent studies have hinted at a much greater role for inflammatory pathways in OA pathology than envisioned previously. Our studies therefore provide new insights into the molecular mechanisms that underlie cartilage response to inflammatory cues during development and aging. Identification of factors like CD24 will help understand how aging and an increase in environmental inflammation with aging can be a trigger for cartilage diseases such as RA and OA. Inhibition of inflammatory modulators like CD24 can also constitute novel therapeutic targets in these cartilage degenerative diseases. In addition, our studies highlight that a major benefit of utilizing human iPSC-based cellular therapies for cartilage repair will be the low immune-responsiveness of the human iPSC-derived chondrocytes especially in the highly inflammatory end-stage environment in RA and OA.

While the preferred embodiments of the invention have been illustrated and described, it will be appreciated that various changes can be made therein without departing from the spirit and scope of the invention.

What is claimed is:

1. A method of enriching for chondrocytes having regenerative potential for cartilage repair, the method comprising:
   a) providing a sample comprising chondrocytes; and
   b) enriching for chondrocytes carrying a CD24 surface marker.

2. The method of claim 1, wherein enriching for the chondrocytes carrying the CD24 surface marker comprises performing fluorescence-activated cell sorting, magnetic-activated cell sorting, single cell sorting, affinity chromatography, or microfluidic cell separation.

3. The method of claim 1, wherein the chondrocytes are neonatal chondrocytes, juvenile chondrocytes, adult chondrocytes, or chondrocytes derived from stem cells.

4. The method of claim 3, wherein the stem cells are pluripotent stem cells.

5. The method of claim 1, wherein the chondrocytes are from a human subject.

6. The method of claim 1, wherein the chondrocytes are xenogeneic, autologous, or allogeneic.

7. The method of claim 1, further comprising culturing the chondrocytes carrying the CD24 surface marker under conditions in which the chondrocytes proliferate.

8. The method of claim 1, wherein the chondrocytes carrying the CD24 surface marker are substantially purified chondrocytes carrying the CD24 surface marker.

* * * * *